United States Patent
Irie et al.

(10) Patent No.: US 7,078,458 B2
(45) Date of Patent: Jul. 18, 2006

(54) METHOD FOR PRODUCTION OF HYDROPHILIC RESIN

(75) Inventors: Yoshio Irie, Himeji (JP); Katsuhiro Kajikawa, Himeji (JP); Kunihiko Ishizaki, Suita (JP); Takumi Hatsuda, Himeji (JP)

(73) Assignee: Nippon Shokubai Co., Ltd., Osaka (JP)

( * ) Notice: Subject to any disclaimer, the term of this patent is extended or adjusted under 35 U.S.C. 154(b) by 0 days.

(21) Appl. No.: 11/014,969

(22) Filed: Dec. 20, 2004

(65) Prior Publication Data

US 2005/0113542 A1 May 26, 2005

Related U.S. Application Data

(60) Division of application No. 10/108,572, filed on Mar. 29, 2002, now Pat. No. 6,998,447, which is a division of application No. 08/427,734, filed on Apr. 24, 1995, now Pat. No. 6,388,000, which is a continuation of application No. 08/074,455, filed on Jun. 10, 1993, now abandoned.

(30) Foreign Application Priority Data

| Jun. 10, 1992 | (JP) | ................................. 4-150425 |
| Oct. 12, 1992 | (JP) | ................................. 4-272789 |

(51) Int. Cl.
*C08L 31/00* (2006.01)
*C08F 20/06* (2006.01)

(52) U.S. Cl. .................... 524/556; 528/503; 525/329.7; 525/330.2

(58) Field of Classification Search ................ 528/272, 528/290, 306, 288, 289, 296, 299, 503; 424/426, 424/85.7, 85.2, 85.4; 524/556; 525/329.7, 525/330.2
See application file for complete search history.

(56) References Cited

U.S. PATENT DOCUMENTS

| 2,026,894 | A | | 1/1936 | Blackley |
| 4,317,926 | A | * | 3/1982 | Sato et al. ................... 562/532 |
| 4,497,930 | A | | 2/1985 | Yamasaki et al. |
| 4,666,983 | A | | 5/1987 | Tsubatimoto et al. |
| 4,708,985 | A | | 11/1987 | Diamantoglou et al. |
| 4,734,478 | A | * | 3/1988 | Tsubakimoto et al. ...... 527/300 |
| 4,808,637 | A | * | 2/1989 | Boardman et al. ......... 521/50.5 |
| 4,920,202 | A | * | 4/1990 | Irie et al. .................... 528/500 |
| 4,929,717 | A | * | 5/1990 | Chmelir ....................... 528/490 |
| 4,985,514 | A | | 1/1991 | Kimura et al. |
| 5,005,771 | A | * | 4/1991 | Pieh et al. ..................... 241/23 |
| 5,061,259 | A | | 10/1991 | Goldman et al. |
| 5,075,344 | A | * | 12/1991 | Johnson ....................... 521/140 |
| 5,079,034 | A | | 1/1992 | Miyake et al. |
| 5,115,011 | A | | 5/1992 | Harada et al. |
| 5,145,906 | A | * | 9/1992 | Chambers et al. .......... 524/732 |
| 5,147,343 | A | | 9/1992 | Kellenberger |
| 5,149,335 | A | | 9/1992 | Kellenberger et al. |
| 5,210,298 | A | | 5/1993 | Shimomura et al. |
| 5,223,569 | A | * | 6/1993 | Schmid ....................... 524/734 |
| 5,229,488 | A | * | 7/1993 | Nagasuna et al. .......... 528/487 |
| 5,241,011 | A | | 8/1993 | Landscheidt et al. |
| 5,244,735 | A | * | 9/1993 | Kimura et al. ............... 428/402 |
| 5,338,810 | A | | 8/1994 | Shimomura et al. |
| 5,455,284 | A | | 10/1995 | Dahmen et al. |
| 5,599,335 | A | | 2/1997 | Goldman et al. |
| 6,114,495 | A | * | 9/2000 | Kolstad et al. ............. 528/354 |
| 6,348,638 | B1 | * | 2/2002 | Schliephake et al. ....... 588/320 |
| 6,388,000 | B1 | | 5/2002 | Irie |
| 6,872,799 | B1 | * | 3/2005 | Nathan ....................... 528/272 |

FOREIGN PATENT DOCUMENTS

| DE | 33 14019 A1 | 1/1984 |
| DE | 33 31 644 A1 | 3/1984 |
| DE | 3545250 A1 | 6/1987 |
| DE | 37 24709 A1 | 2/1989 |
| DE | 4004953 A1 | 8/1991 |
| DE | 4021847 A1 | 1/1992 |
| EP | 0 083 022 A2 | 7/1983 |
| EP | 0 295 438 A2 | 12/1988 |
| EP | 0 303 518 A2 | 2/1989 |
| EP | 0 304 319 A2 | 2/1989 |
| EP | 0 339 461 A1 | 11/1989 |
| EP | 0372706 A2 | 6/1990 |
| EP | 0 441 975 A1 | 8/1991 |

(Continued)

OTHER PUBLICATIONS

Wampler III, Francis M., "*Formation of Diacrylic Acid During Acrylic Acid Storage*," Plant/Operations Progress, vol. 7, No. 3, pp. 183-189, Jul. 1988.

(Continued)

*Primary Examiner*—Helen L. Pezzuto
(74) *Attorney, Agent, or Firm*—Buchanan Ingersoll PC

(57) ABSTRACT

In the production of an acrylate polymer by the steps of preparing a water-soluble unsaturated monomer having a ratio of neutralization in the range of 30 to 100 mol % and containing 50 to 100 mol % of an acrylate and then polymerizing the monomer, a method for the production of a hydrophilic resin which comprises using a water-soluble unsaturated monomer having a β-hydroxy propionic acid (salt) content of not more than 1,000 ppm. The hydrophilic resin obtained by this method exhibits excellent physical properties and has only a small residual monomer content. Further, a residual monomer content neither occurs nor increases in any using conditions.

19 Claims, No Drawings

FOREIGN PATENT DOCUMENTS

| | | |
|---|---|---|
| EP | 0 509 708 A1 | 10/1992 |
| GB | 2058801 A | 4/1981 |
| JP | 49-30312 | 3/1974 |
| JP | 50-15881 | 2/1975 |
| JP | 50-142511 | 11/1975 |
| JP | 55-094334 | 7/1980 |
| JP | 57-44627 A | 3/1982 |
| JP | 58-117222 A | 7/1983 |
| JP | 58-183754 A | 10/1983 |
| JP | 58-180223 A | 12/1983 |
| JP | 61-016903 A | 1/1986 |
| JP | 63-302941 | 12/1988 |
| JP | 2-253845 A | 10/1990 |
| JP | 63-31306 A | 2/1991 |
| JP | 4-106108 A | 4/1992 |
| WO | WO90/15825 A1 | 12/1990 |

OTHER PUBLICATIONS

Cutie, S.S. et al., "*Separation and characterization of acrylic acid oligomers by nuclear magnetic resonance spectroscopy and thermospray ion-exchange liquid chromatography-mass spectrometry,*" Journal of Chromat., The Dow Chemical Company, pp. 349-355, (Rec'd Jun. 16, 1987).

Prager, Bernhard et al., "*Beilsteins Handbuch der Organischen Chemie,*" Verlin, Verlag von Mulius Sporinger, pp. 295-297, 1921.

Elvers, Barbara et al., "High-Performance Fibers to Imidazole and Derivatives," Ullmann' Encyclopedia of Industrial Chemistry, Fifth, Completely Revised Edition, vol. A13, pp. 508-514, 1989.

Mailing No. 165786, Official Action mailed Jun. 13, 2000, pp. 1-3; with Translatioin, pp. 1-3.

Mailing No. 279923, Official Action mailed Oct. 3, 2000, pp. 1-2; with Translation pp. 1-3.

Search Report in corresponding European Patent Application No. 98 202 710.4-2109 dated Sep. 25, 2001.

Masuda, "*High Absorbent Polymer*", pp. 64-73 (with partial translation), Jun. 1, 1997.

Acrylic Ester Industrial Association, "*Acrylic Acid and Acrylic Esters, Safety Instruction for Treatment*", 4th Edition, pp. 16-19 (with partial translation), Apr. 1992.

Shuppan, Encyclopedia Chimica 7 (with partial translation), pp. 440-441, Mar. 15, 1969.

Ohmori, Acrylic Acid and Polymer Thereof—Mainly about industrial use, pp. 34-36, Jun. 30, 1976.

Patent Opposition, against corresponding Japanese Patent No. 3,349,768, Appln. No. 5-137,580 (with translation); May 23, 2003.

Decision on Opposition, with translation (excluding list of evidences).

Demand for Appeal, with translation (excluding list of evidences).

Report of Experiment, with partial translation, Jul. 25, 2003.

Kilburn & Strode—communication with attached translation of opposition statement, Feb. 1, 2000.

Kilburn & Strode—communication constituting counter-statement to opposition, Aug. 9, 2000.

Communication from Luderschmidt, Schüler & Partner to Hatta & Associates with attached draft of patentees' statement, Aug. 13, 2003.

Communication from Luderschmidt, Schüler & Partner to Hatta & Associates enclosing translation of modified opposition statement, Dec. 23, 2003.

Communication from Luderschmidt, Schüler & Partner to Hatta & Associates enclosing translation of reply to opposition, Apr. 22, 2004.

Declaration by Günther Bub with translation, Jul. 25, 2003.

Declaration by Dr. Heinz-Peter Bohlmann with translation, Jul. 25, 2003.

Affidavit of Dr. Franck Furno, Apr. 11, 2005 Opposition against EP 0574 260 B1.

Buchholz, Frederic L. et al., "*Modern Superabsorbent Polymer Technology*", Wiley-VCH (1998). pp. 75 and 114.

Walter, Wolfgang, "*Beyer-Walter, Schoolbook of Organic Chemistry*", S. Hirzel Verlag, Stuttgart, Germany (1988) p. 281.

* cited by examiner

METHOD FOR PRODUCTION OF HYDROPHILIC RESIN

CROSS-REFERENCE TO RELATED APPLICATION

The present application is a divisional of U.S. application, Ser. No. 10/108,572, filed Mar. 29, 2002, now U.S. Pat. No. 6,998,447 which, in turn, is a divisional of Ser. No. 08/427,734, filed Apr. 24, 1995, now U.S. Pat. No. 6,388,000, which, in turn, is a continuation of abandoned application, Ser. No. 08/074,455, filed Jun. 10, 1993.

BACKGROUND OF THE INVENTION

1. Field of the Invention

This invention relates to a method for the production of a hydrophilic resin having an acrylate as a main component thereof. More particularly it relates to a method for the production of a hydrophilic resin which has only a small residual monomer content and shows virtually no increase in the residual monomer content under varying conditions of use.

The hydrophilic resin according to this invention can be produced easily and inexpensively and is excellent in quality and safety and therefore, can be used as an absorbent resin and water-soluble resin in a wide range of applications.

2. Description of the Prior Art

The hydrophilic resins can be generally classified by their solubility in water into roughly two types, water-soluble resins and absorbent resins.

Water-soluble resins are hydrophilic resins of the type which dissolve in water and are used, for example, as water treatment grade flocculants, oil drilling additives, food additives, and viscosity enhancers.

The water-soluble resins which are known to this art include, for example, polysodium acrylate (JP-B-48-42,466 and JP-B-42-9,656), polyacrylic acid and polyacrylamide (JP-A-54-145,782 and JP-A-57-18,652), polymers of 2-acrylamide-2-methylpropane sulfonic acid (JP-A-2-173,108), partial hydrolysate of polyacrylamide (JP-A-52-137,483), acrylic acid-acrylamide copolymer (JP-A-59-15,417), (meth)acrylic acid-acrylic acid copolymer (JP-A-59-15,417), (meth)acrylic acid-itaconic acid copolymer (JP-A-58-91,709), and polyvinyl alcohol.

Absorbent resins are water-insoluble hydrophilic resins of the type which absorb water and consequently undergo gelation and are widely used in the fields of agriculture and forestry and in the field of civil engineering as well as in the field of hygienic materials such as disposable diapers and sanitary napkins.

The absorbent resins which have been heretofore known include, for example, partially neutralized cross-linked polyacrylic acid (JP-A-55-84,304, JP-A-55-108,407, and JP-A-55-133,413), hydrolyzate of starch-acrylonitrile graft polymer (JP-A-46-43,995), neutralized starch-acrylic acid graft polymer (JP-A-51-125,468), saponified vinyl acetate-acrylic ester copolymer (JP-A-52-14,689), hydrolyzate of acrylonitrile copolymer or acrylamide copolymer (JP-A-53-15,959) or cross-linked derivatives thereof, and cross-linked cationic monomer (JP-A-58-154,709 and JP-A-58-154,710).

Numerous compounds have been proposed as monomers for the production of these hydrophilic resins. From the viewpoint of the quality of the product and the cost of production, a partially or completely neutralized acrylate (hereinafter referred to as "acrylate") is predominately used today. The acrylate type polymers which have acrylates as the main component of their monomers are produced today in large amounts for both absorbent resins and water-soluble resins and have been finding extensive utility in the fields of hygienic materials and foodstuffs.

By the current technical standard, it is normal that the acrylate type polymers which are in wide use generally contain such a residual monomer as unaltered acrylic acid (or a salt thereof) in a concentration in the range of 500 to 3,000 ppm. Thus, the desirability of decreasing the residual monomer content in the polymers has been finding enthusiastic recognition.

In these hydrophilic resins, particularly the absorbent resins used in sanitary materials, a lower the residual monomer content is required. In recent years, the prevailing demand is to lower the residual monomer content to below 100 ppm. This decrease of the residual monomer content is particularly difficult to attain in the absorbent resins among the hydrophilic resins because the absorbent resins are hydrophilic resins of the type having a cross-linked structure and, therefore, more often than not have a neutral pH value.

The absorbent resins having a cross-linked structure are not easily polymerized uniformly as compared with water-soluble resins. When absorbent resins fresh from polymerization are to be mixed with an additive to decrease the residual monomer content or with an organic solvent, a uniform mixture is not easily obtained because of the cross-linked structure of the polymers. Thus, a decrease of the residual monomer content in the absorbent resins has been extremely difficult to attain. Moreover, since acrylates are such that their polymerization velocities are lowered proportionately as their pH values approach neutrality, a decrease of the residual monomer content as a consequence of polymerization has been extremely difficult to attain in neutral acrylate type absorbent resins.

Heretofore, in the field of macromolecular flocculants, for example, there has been an attempt at decreasing the residual monomer content in hydrophilic resins. Even now, numerous hydro-philic resins mentioned above as well as acrylate type polymers and absorbent resins are still the subjects of a study in a search for measures of decreasing the residual monomer content.

The techniques known to the art are broadly divided into the following six types (a) to (f):

(a) Methods for lowering the residual monomer content by increasing the polymerization ratio of the polymer itself.

The methods of this type include, for example, increase of the amount of polymerization initiator and the use of a composite initiator (JP-A-50-96,689), elevation of the reaction temperature, an increase in the polymerization concentration, lengthening the polymerization time, and the specification of aging conditions (JP-A-53-145,895), the two-stage addition of a polymerization initiator (JP-A-56-72,005), the exposure of a resin fresh from polymerization to radiation (JP-A-63-43,930), and the irradiation of a resin fresh from polymerization with ultraviolet light (JP-A-62-260,906).

(b) Methods for converting the residual monomer in the polymer into an extraneous derivative by use of an additive.

The methods of this type include, for example, the subsequent addition of a primary or secondary amine (JP-A-50-40,649), the subsequent addition of sulfur dioxide (U.S. Pat. No. 3,780,006), and the subsequent addition of an alkali metabisulfite (U.S. Pat. No. 4,306,955).

(c) Methods for extracting the residual monomer from the polymer.

The methods of this type include, for example, the extraction by the use of a hydrophilic organic solvent (U.S. Pat. No. 4,794,116) and the supercritical extraction by the use of carbon dioxide.

(d) Methods for treating the residual monomer with a micro-organism capable of decomposing the residual monomer The methods of this type include, for example, decomposition of residual acrylamide with a microorganism (U.S. Pat. No. 4,742,114).

(e) Methods for volatilizing the residual monomer at elevated temperatures

The methods of this type include, for example, volatilization of residual acrylonitrile at an elevated temperature (JP-A-54-119,588).

The methods of (a), however, are actually such that since their effects in lowering the residual monomer content are not sufficient, the residual monomer generally persists in a concentration of at least 0.03% and the self-cross linking occurs and basic molecular weight of the hydrophilic resin are necessarily degraded by the harsh conditions during polymerization and the aftertreatment possibly to the extent of increasing the water-soluble content of the absorbent resin, lowering the gel strength, and impairing the physical properties of the resulting hydrophilic resin.

Further, the two-stage addition of a polymerization initiator and the use of a large amount of initiator increases the possibility of the polymerization initiator persisting in the produced resin and consequently jeopardizing the safety of the produced polymer.

The methods of (b) and (c) are purportedly capable of lowering the residual monomer content to below 0.03%. However in (b), in addition to complexed process, an additive used and the adduct formed of the additive with the residual monomer and in (c) the organic solvent such as methanol used for the extraction of residual monomer, never fail to persist in the hydrophilic resin.

The effect of the method of (c) in lowering the residual monomer content in the resin, however, is limited because acrylates are not dissolved in such organic solvents as methanol.

The method of (d) is not easily carried out on a commercial scale because of the use of a microorganism. Moreover, the use of the microorganism itself proves to be undesirable from the standpoint of safety.

The method of (e) is observed at times to impair various physical properties by the elevated temperatures. Moreover, since the acrylate fails to volatilize even at elevated temperatures, this method can hardly be expected to attain an effective decrease of the residual monomer content.

More recently, (f) the efforts directed to the reduction of the residual monomer content have revealed in the water-soluble unsaturated monomer as a matter deserving due attention before polymerization. The method embodying this knowledge has also been known to the art.

The methods of this type already known to the art include polymerization effected by the use of an acrylate obtained by a specific method of neutralization (EP-A-0372706) and polymeri-zation attained by the use of a monomer having a small heavy metal content (JP-A-3-31,306), for example.

The methods of the type of (f), however, are not sufficiently effective in lowering the residual monomer content.

The methods of the various types cited above, however, are actually such that they not only fail to produce the required effect but also necessitate a complicated process and involve a sacrifice in productivity and physical properties and a large addition to the cost of production. Moreover, these methods only bring about an apparent decrease in the residual monomer content in the acrylate type polymer and are totally incapable of repressing the increase of the residual monomer content which occurs subsequent to the polymerization as described hereinbelow.

We have found that in the acrylate polymer which is obtained by the conventional method, an unaltered monomer persists in such high concentrations as to fall in the approximate range of some tens of ppm to some thousands of ppm in addition to the residual monomer of the type generally known in the art. We have also found that even when the residual monomer content of the acrylate polymer is decreased apparently to a level of some hundreds of ppm, the residual monomer actually increases proportionately over a period of time. This increase over a period of time is particularly conspicuous when the polymer is heated.

When the acrylate polymer having an apparently small residual monomer content is required to undergo further heating or when it is used in an agronomic field for a long time or exposed to an elevated temperature such as, for example, hot water, it is natural to conclude that this use of the polymer is undesirable from the viewpoint of safety because the residual monomer content is increased under such conditions of use.

Concerning the production of the acrylate polymer, many techniques have been known to cross-link the surface region of the acrylate polymer for the purpose of improving the various physical properties thereof besides the mere operations of polymerization and drying. Particularly in the field of absorbent resins, various surface cross-linking agents and reaction conditions for surface cross-linking have been proposed because cross-linking near the surface region exerts numerous effects on the physical properties of the absorbent resin.

The methods for surface cross-linking the acrylate polymer by the use of specific surface cross-linking agents heretofore known to the art include, for example, a method using a polyhydric alcohol (JP-A-58-180,233 and JP-A-61-16,903), a method using an alkylene carbonate (DE-4020780C), a method using glyoxal (JP-A-52-117,393), a method using a polyvalent metal (JP-A-51-136,588, JP-A-61-257,235, and JP-A-62-7,745), and a method using a silane coupling agent (JP-A-61-211,305, JP-A-61-252,212, and JP-A-61-264,006). The methods for surface cross-linking the resin under specific reaction conditions which have been hereto-fore known to the art include, for example, a method effecting the desired cross-linking by dispersing an absorbent resin in a mixed solvent consisting of water and a hydrophilic organic solvent (JP-A-57-44,617), a method effecting the cross-linking by dispersing an absorbent resin in an inert medium in the presence of a specific amount of water (JP-A-58-117,222), a method effecting the cross-linking by establishing co-existence of an inorganic powder and water (U.S. Pat. No. 45,687,308), and a method resorting to exposure of the polymer to an electromagnetic radiation (JP-A-63-43,930).

The various methods thus proposed, however, are invariably incapable of sufficiently improving the various physical properties of the acrylate polymer by surface cross-linking. Thus, studies are still continuing to attain thorough improvement of the physical properties.

In the process of studying an improvement of the surface cross-linking of the acrylate polymer, we have found the heretofore totally unknown fact that surface cross-linking markedly increases the residual monomer content in the acrylate polymer to a level in the approximate range of some tens of ppm to some hundreds of ppm and that the increase of the residual monomer content due to surface cross-linking accounts for a large proportion of the residual monomer content in the final product.

In a hydrophilic resin of an acrylate polymer which does not easily allow a decrease of the residual monomer content and has the peculiar phenomenon of newly generating residual monomer or increasing the amount of already existent residual monomer in the polymer during manufacture of the resin or during use of the resin, this invention has an object of providing a method for the production of a hydrophilic resin having excellent physical properties, having only a small residual monomer content, and showing virtually no sign of generation or augmentation of residual monomer after polymerization.

In a hydrophilic resin of an acrylate polymer which has various physical properties improved by cross-linking the surface region thereof, this invention has another object of providing a method for the production of a hydrophilic resin which has the surface region thereof cross-linked and is consequently able to have a noticeable effect in improving various physical properties and enjoys a notable decrease in the residual monomer content thereof.

SUMMARY OF THE INVENTION

The objects described above are attained by a method for the production of a hydrophilic resin which comprises polymerizing a water-soluble unsaturated monomer containing 50 to 100 mol % of an acrylate having a neutralization ratio in the range of 30 to 100 mol % and not more than 1,000 ppm of β-hydroxy propionic acid (salt).

These objects are also accomplished by a method for the production of a hydrophilic resin which comprises polymerizing a water-soluble unsaturated monomer containing 50 to 100 mol % of an acrylate having a neutralization ratio in the range of 30 to 100 mol % and not more than 1,000 ppm of β-hydroxy propionic acid (salt) and treating the surface region of the resultant acrylate polymer with a second cross-linking agent having in the molecular unit thereof at least a group capable of reacting with the functional group of the aforementioned acrylate polymer, thereby cross-linking the surface region.

These objects are also accomplished by an acrylic acid polymer composition which contains 1–1000 ppm of β-hydroxy propionic acid (salt) and not more than 100 ppm of a residual monomer.

As a result of a diligent study made for the purpose of accomplishing the objects described above, we have ascertained the fact that a hydrophilic resin having a high residual monomer content and a hydrophilic resin in which the residual monomer greatly increases contain about several 1000 ppm to 1% of β-hydroxy propionic acid (salt) as a trace element in addition to the residual monomer. We have also found that the β-hydroxy propionic acid content and the residual monomer content are related.

As a means to solve the problem, we have taken note of the β-hydroxy propionic acid (salt) contained in a small amount in the acrylic acid (or salt thereof) monomer. This correlation has never drawn any attention to date. We have succeeded in solving the various problems mentioned above by adopting a measure to control the content of this trace element. This invention has been perfected as a result.

The method of production contemplated by this invention has the following characteristic features (1) to (5).

(1) The residual monomer content which has heretofore been decreased by a complicated treatment such as by the use of an additive with a resulting sacrifice in its properties, productivity, cost, and safety of the acrylate polymer, can now be decreased by a simple procedure.

(2) Since the increase of the residual monomer content in the polymer during production is small, even when an elevated temperature is used in the process a polymer can be obtained with a high operational efficiency. Further, since the reaction can be carried out at high temperatures, a large number of physical properties superior in high absorption capacity of the polymer can be notably improved.

(3) Since there is little possible generation and increase of the residual monomer content in the polymer during protracted use or at an elevated temperature, the product enjoys a high level of safety under all conditions such as, for example, those involved in protracted agronomic use and in use at the elevated temperature of hot water.

(4) The residual monomer content of the polymer can be decreased for the purpose of enhancing the properties of the polymer even with a small amount of catalyst or under mild polymerization conditions, and an acrylate polymer can be obtained with still better performance without sacrificing physical properties.

(5) Virtually no increase of the residual monomer content in the polymer is observed while the polymer is undergoing surface cross-linking treatment and the effect of the surface treatment can be also improved.

The acrylate polymer obtained as described above can be utilized extensively in various fields covering, for example, sanitary materials, foodstuffs, civil engineering, and agriculture.

DESCRIPTION OF THE PREFERRED EMBODIMENT

Now, this invention will be described more specifically below.

For this invention, it is essential that the proportion of the acrylate in the water-soluble unsaturated monomer to be used for polymerization be in the range of 50 to 100 mol %. The term "acrylate" as used in this invention refers to the total of acrylic acid and an acrylate.

Since the effects of this invention in lowering the residual monomer content of the polymer is produced proportionately as the proportion of acrylate in the water-soluble unsaturated monomer increases, the proportion of the acrylate in the water-soluble unsaturated monomer of this invention is preferably in the range of 70 to 100 mol %, more preferably in the range of 90 to 100 mol %. If the content of the acrylate is less than 50 mol %, the shortage of supply has the disadvantage in not only degrading the quality of the product and boosting the cost of production but also making it difficult to produce the effects of this invention and, depending on situation, increasing rather than decreasing the residual monomer content.

It is also essential that the neutralization ratio of the acrylate which is used for the preparation of the water-soluble unsaturated monomer be in the range of 30 to 100 mol %. If this ratio is less than 30 mol %, the produced acrylate polymer possibly produces excessive acidity and suffers from an increase of the residual monomer content. Conversely, if the ratio of neutralization exceeds 100 mol %, the produced acrylate polymer has the disadvantage of producing excessive basicity and an increase of the residual monomer content.

The effect which the water-soluble unsaturated monomer used in this invention brings about in lowering the residual monomer content of the produced polymer is produced more noticeably when neutralization of the monomer is partial than perfect neutralization. When the water-soluble unsaturated monomer of this invention is used, the ratio of neutralization at which the residual monomer content is lowered as compared with the conventional method is preferably in the range of 40 to 95 mol %, more preferably in the range of 50 to 85 mol %. The expression "ratio of neutralization of the acrylate" as used in this invention refers to the ratio of neutralization of the acrylate used for the preparation of the water-soluble unsaturated monomer or to the ratio of neutralization of the acrylate in the water-soluble monomer after this monomer has been mixed, as the situation demands, with other monomer.

The water-soluble unsaturated monomer used for this invention contains 50 to 100 mol % of an acrylate having a ratio of neutralization in the range of 30 to 100 mol %. Optionally, it may use 0 to 50 mol % of a hydrophilic unsaturated monomer and/or a hydrophobic unsaturated monomer in addition to the acrylate mentioned above.

As concrete examples of the hydrophilic unsaturated monomer which can be used optionally in an amount in the range of 0 to 50 mol %, acid group-containing hydrophilic unsaturated monomers such as methacrylic acid, maleic acid, maleic anhydride, fumaric acid, crotonic acid, itaconic acid, vinyl sulfonic acid, styrene sulfonic acid, 2-(meth)acrylamide-2-methylpropane sulfonic acid, 2-(meth)acryloyl ethane sulfonic acid, and 2-(meth)acryloyl propane sulfonic acid and salts thereof; nonionic hydrophilic unsaturated monomers such as acrylamide, methacrylamide, N-ethyl (meth)acrylamide, N-n-propyl (meth)acrylamide, N-isopropyl (meth)acrylamide, N,N-methyl (meth)acrylamide, 2-hydroxyethyl (meth)acrylate, 2-hydroxypropyl (meth)acrylate, methoxy poly-ethylene glycol (meth)acrylate, polyethylene glycol (meth)-acrylate, vinyl pyridine, N-vinyl pyrrolidone, and N-acryloyl piperidine; and cationic hydrophilic unsaturated monomers such as N,N-dimethyl amino ethyl (meth)acrylate, N,N-diethyl amino ethyl (meth) acrylate, N,N-dimethyl amino propyl (meth)acrylate, N,N-dimethyl amino propyl (meth)acrylamide, and quaternary salts thereof may be cited. One member or a combination of two or more members selected from the group of hydrophilic unsaturated monomers cited above may be used. Such an unsaturated monomer as methyl (meth)acrylate, ethyl (meth)acrylate, or vinyl acetate which forms a hydrophilic resin by hydrolysis of the functional group thereof may be used herein.

Among other examples cited above of the hydrophilic unsaturated monomer which is used in an amount in the range of 0 to 50 mol % in this invention, methacrylic acid (salt thereof), 2-(meth)acryloyl ethane sulfonic acid (salt thereof), 2-(meth)-acrylamide-2-methyl propane sulfonic acid (salt thereof), methoxy polyethylene glycol (meth) acrylate, N,N-dimethylaminoethyl (meth)acrylate, and acrylamide prove to be particularly preferable.

As concrete examples of the hydrophobic unsaturated monomer which is optionally used in an amount in the range of 0 to 50 mol %, styrene, vinyl chloride, butadiene, isobutene, ethylene, propylene, stearyl (meth)acrylate, and lauryl (meth)acrylate may be cited. The hydrophobic unsaturated monomer is used in an amount in the range of 0 to 50 mol %, preferably 0 to 20 mol %, and more preferably 0 to 10 mol %, based on the total amount of monomers.

The neutralization of the water-soluble unsaturated monomer containing 50 to 100 mol % of an acrylate having a ratio of neutralization in the range of 30 to 100 mol % may be carried out during the preparation of the water-soluble unsaturated monomer or during or after the polymerization.

In this invention, for the preparation of the water-soluble unsaturated monomer containing 50 to 100 mol % of an acrylate having a ratio of neutralization in the range of 30 to 100 mol % as described above, it is essential that the produced water-soluble unsaturated monomer should contain β-hydroxy propionic acid and a salt thereof (hereinafter both collectively referred to simply as "β-hydroxy propionic acid") in an amount of not more than 1,000 ppm, based on the amount of the water-soluble unsaturated monomer.

For this invention, the content of the β-hydroxy propionic acid in the water-soluble unsaturated monomer should be not more than 1,000 ppm, preferably not more than 500 ppm, and more preferably not more than 300 ppm, most preferably not more than 100 ppm, based on the amount of solids.

The β-hydroxy proprionic acid content of the order of 1 to 10 ppm is not particularly intolerable. The effort to lower the β-hydroxy proprionic acid content to below 1 ppm proves to be rather uneconomical.

If the content of the β-hydroxy propionic acid in the water-soluble unsaturated monomer exceeds 1,000 ppm, the acrylate polymer to be obtained by polymerization of the water-soluble unsaturated monomer is at a disadvantage in that it has an unduly large residual monomer content and, while the polymer is undergoing the subsequent heat treatment or being used at an elevated temperature, the polymer produces the phenomenon of newly generating residual monomer or increasing the already existent residual monomer content and, while the acrylate polymer is undergoing a surface cross-linking treatment, this polymer prevents the surface cross-linking treatment from having the effect of improving various physical properties of the polymer.

The reason for the association of the content of β-hydroxy propionic acid in the polymer with an increase of the residual monomer content or the generation and growth of residual monomer in the polymer after drying remains yet to be determined. A forced inference is that since the sodium salt of β-hydroxy propionic acid has a melting point (143° C.), when the polymer obtained from the monomer containing much more β-hydroxy propionic acid and further since the acrylate polymer generates or increases a large amount of residual monomer even at a temperature lower than the melting point of the salts of β-hydroxy propionic acid, the β-hydroxy propionic acid in the acrylate polymer in the solid state is far more decomposable than the β-hydroxy propionic acid in its independent form or the β-hydroxy propionic acid possibly inhibits polymerization or promotes depolymerization of the acrylate polymer after the polymerization step.

For this invention, the content of the β-hydroxy propionic acid in the water-soluble unsaturated monomer when polymerization is initiated is only required to be limited to below 1,000 ppm. The procedure used for the preparation of the water-soluble unsaturated monomer of this description is not specifically limited.

One typical example of the procedure for the preparation of this water-soluble unsaturated monomer is cited below.

Acrylic acid is refined by distillation and then subjected to neutralization or put to use for the preparation of a monomer as soon as possible, specifically within a period of 24 hours, preferably 12 hours, and more preferably 6 hours. In the process of neutralization, the refined acrylic acid, at least for a while, passes the state in which the ratio of neutraliza-tion exceeds 100 mol %. Then, the acrylic acid is used to adjust the ratio of neutralization at a prescribed level and when necessary a second monomer is added to obtain the monomer as the component for polymerization. As soon as possible the monomer thus obtained is subjected to polymerization, specifically within a period of 24 hours, preferably 12 hours, more preferably 6 hours, and particularly preferably 2 hours, after the preparation of the monomer. The acrylic acid fresh from the refinement by distillation is preferably kept at the lowest possible temperature, specifically below 30° C., preferably between the solidifying point and 25° C., until it is subjected to neutralization or put to use for the preparation of the monomer. The neutralization is preferably carried out at a low tempera-ture for a brief period. When the acrylic acid resulting from the distillation is left standing for a relatively long time, it is preferably kept in an anhydrous state. Further, the monomer which has been prepared ought to be stored at a tempera-ture in the range between the solidifying point thereof and 40° C., preferably between 0° C. and 30° C. If the storage temperatures of acrylic acid and the monomers are high, an amount of β-hydroxy propionic acid and the residual monomer sometimes increase, so it is not preferable.

Acrylic acid is finally distilled and put to storage at an acrylic acid manufactory and subsequently shipped out. It takes at least four to five days and more generally some tens of days to some months before it is put to actual use on a commercial scale by the consumer. The monomer is prepared in a large amount at a factory and then put to storage in the plant. An average of not less than three days elapses after the preparation of the monomer is completed and before it is put to actual use. More-over, in preparation for the polymerization, the monomer required several hours for the deaeration treatment of and temperature adjustment. We have found that the amounts of β-hydroxy propionic acid and residual monomer increase proportionately as the time after the refinement of acrylic acid by distillation increases and the time after completion of the preparation of the monomer and before the monomer is put to polymerization increases. For the present invention, therefore, the monomer fresh monomer is preferably produced just after distillation in a short time, and also the monomer fresh from its preparation is preferably polymerized as soon as possible.

Of the various methods which are available for neutralizing acrylic acid under the condition of causing the acrylic acid at least for a while to pass the state in which the ratio of neutralization exceeds 100 mol %, (1) the most convenient method comprises keeping the system of neutralization reaction cooled and simultaneously gradually adding a acrylic acid to a fixed amount of basic substance.

As another method which is available for the same purpose, (2) the method as disclosed in JP-A-2-209,906 and EP-A-0372706 may be cited. The method comprises allowing the ratio of neutralization of the acrylate in the system of neutralization to remain below 100 mol % from the start of the neutralization, then causing the acrylate in the process of neutralization to pass the stage in which the ratio of neutralization exceeds 100 mol %, and finally adjusting the ratio of neutralization to a level in the range of 30 to 100 mol %. The method of (1) sacrifices the velocity of neutraliza-tion and necessitates a low temperature for the decrease of β-hydroxy propionic acid. The method of (2) fails to attain a decrease of β-hydroxy propionic acid content with high operational efficiency so long as it uses the aforementioned acrylic acid.

From the standpoint of the various physical properties of the produced absorbent resin and the residual monomer remaining in the resin. This invention contemplates partially or wholly neutralizing such an acid radical-containing monomer as acrylic acid.

The basic substances which can be effectively used for the neutralization of the monomer include, for example, (hydrogen) carbonates and hydroxides of alkali metals, ammonia, and various amino acids such as alanine, and organic amines. Among other basic substances, sodium hydroxide and/or potassium hydroxide prove to be preferable and sodium hydroxide prove to be more preferable from the viewpoint of the various physical properties and a decrease of the residual monomer content. Further, if ammonia is used together with NaOH/KOH in the present invention, the residual monomer can be more highly decreased. The monomer may incorporate therein, urea as an ammonia precursor before it is polymerized. The gel polymer obtained from the partially neutralized monomer is not necessarily prohibited from being further neutralized during or after polymerization. When such a strong base as sodium hydroxide is used for the after neutralization, due attention must be paid to preclusion of the possible hydrolysis of cross-linking points. When the further neutralization is to be effected by the use of a polyester type cross-linking agent, such a weak base as ammonia or a hydrogen carbonate of an alkali metal is favorably used.

In this invention, in order to more highly decrease the residual monomer, the proportion of an ammonium salt in the base to be neutralized mainly as an alkali metal salt and ammonium salt is in the range of 4 to 50 mol %, preferably 10 to 40 mol %. The proportion of the alkali metal salt in the base is in the range of 10 to 96 mol %, preferably 20 to 80 mol %. So long as these salts are within the relevant ranges mentioned above, the absorbent resin to be obtained entails neither coloration nor the production of any harmful byproducts, suffers from only a small residual monomer content, and excels in various physical properties. The neutralization with an extremely small amount of a polyvalent metal salt constitutes in itself no alteration of the gist of this invention. Further, neutralization is carried by using together with ammonia, in order to decrease the residual monomer, the ranges specified above for the proportions of the relevant salts become highly significant when the gel polymer or a salt thereof is subjected to below mentioned hear-treatment. Thus, the salts may be in amounts below the lower limits of the ranges in the course of polymerization and then adjusted to the proportions falling within the limits prior to heat treatment. The adjustment of these proportions to the ranges mentioned above is conveniently effected preparatorily to polymerization. This particular timing of the adjustment is favorable in that it allows the effect of the surface treatment to be additionally enhanced.

This invention can obtain the absorbent resin by polymerizing and cross-linking the monomer; the β-hydroxy propionic acid content of which is not more than 1,000 ppm as mentioned above.

The method to be adopted for the cross-linking treatment is not particularly discriminated by this invention. For example, a method which comprises polymerizing the monomer of this invention thereby obtaining a water-soluble resin and then cross-linking this resin in the presence of a cross-linking agent added to the resin during or after the polymerization, a method which effects radical cross-linking by the use of a radical polymerization initiator, and a method which effects radical cross-linking by the use of an electron beam may be cited. For the purpose of obtaining an absorbent resin of excellent quality with high operational efficiency, the procedure which comprises polymerizing the monomer to which a cross-linking agent has been added in a prescribed amount prior to polymerization and subjecting the resultant polymer to a cross-linking reaction simultaneously with or subsequently to polymerization proves to be particularly preferred.

As typical examples of the cross-linking agent used in the method which comprises polymerizing the monomer in the presence of a cross-linking agent added in a prescribed amount to the monomer in advance of polymerization and subjecting the resultant polymer to a cross-linking treatment either simultaneously with or subsequently to the polymerization, N,N'-methylene bis-acrylamide, (poly)ethylene glycol di(meth)acrylate, (poly)propylene glycol di(meth)acrylate, trimethylol propane tri(meth)acrylate, trimethylol propane di(meth)acrylate, (poly)-ethylene glycol di(β-acryloyloxy propionate), trimethylol propane tri(β-acryloyloxy propionate), poly(meth)allyloxy alkane, (poly)ethylene glycol diglycidyl ether, ethylene glycol, polyethylene glycol, glycerin, pentaerythritol, ethylene diamine, and polyethylene imine may be cited. The amount of the cross-linking agent to be used is generally in the range of 0.005 to 5 mol %, preferably 0.01 to 1 mol %, based on the amount of monomer. Among the cross-linking agents cited above, it is preferable to use essentially a polymerizing cross-linking agent which has two or more polymerizing unsaturated groups in the molecular unit thereof subject to the durability and absorption characteristics of the absorbent resin to be obtained and the convenience of handling of the hydrated gel during the course of production.

When the monomer is to be polymerized as described above in this invention, although either bulk polymerization or precipita-tion polymerization may be employed, from the viewpoint of the quality of the product and the ease of control of the polymerization step the monomer is preferably polymerized in the form of a solution. The solvent for the polymerization system has no particular restriction except for the sole requirement that it should be a liquid capable of dissolving the monomer. As concrete examples of the solvent, water, methanol, ethanol, acetone, dimethyl formamide, and dimethyl sulfoxide may be cited. Among other solvents which are available at all, water or an aqueous liquid proves to be particularly preferred. Although the concentration of the monomer in the solution may exceed that of a saturated solution, it is generally in the range of 20% by weight to of the concentration of a saturated solution, preferably in the range of 25 to 50% by weight. If the concentration of the monomer is unduly high, due attention should be paid to the avoiding of the otherwise possible degradation of various physical properties of the product.

The monomer ready for polymerization may incorporate therein such water-soluble chain transfer agents as hypophosphites and salts thereof, thiols, and thiolic acid and salts thereof and such hydrophilic polymeric compounds as starch, cellulose, polyvinyl alcohol, polyacrylic acid, and cross-linked polyacrylic acid. Generally, the amount of a water-soluble chain transfer agent is within 5 parts by weight and that of a hydrophilic polymeric compound within 50 parts by weight.

The water-soluble unsaturated monomer having a β-hydroxy propionic acid content of not more than 1,000 ppm which has been obtained as described above is then subjected to polymerization. Further, the water-soluble unsaturated monomer after finishing control is preferably subjected to polymerization as short time as possible as mentioned above.

As typical examples of the method to be adopted by this invention for polymerization, radical polymerization using a radical polymerization initiator and polymerization using an active energy ray such as an ultraviolet light or an electron beam may be cited. In all these methods, radical polymerization by virtue of a radical polymerization initiator is preferred for the purpose of obtaining an acrylate polymer which excels in quality.

By the use of the method of production according to this invention, the water-soluble unsaturated monomer is allowed to acquire improved polymerizability and a decrease of the residual monomer content can be obtained with a radical polymerization initiator used in a smaller amounts than normally required. Thus, the polymerization can be controlled easily and the acrylate polymer can be produced with still better properties.

The radical polymerization initiator used may be any of those known in the art. As typical examples of the radical polymerization initiator which can be used effectively, persulfates such as potassium persulfate, ammonium persulfate, and sodium persulfate; organic peroxides such as t-butyl hydroperoxide and cumene hydroperoxide; hydrogen peroxide; azo compounds such as 2,2'-azo-bis(2-amidinopropane)dihydrochloride; and chlorites, hypochlorites, ceric salts, and permanganates may be cited. Among other radical polymerization initiators cited above, it is preferable to use one or more members selected from the group consisting of persulfates, hydrogen peroxide, and azo compounds from the viewpoint of the quality of the produced acrylate polymer and decreasing of the residual monomer content.

When an oxidizing radical polymerization initiator is used as the polymerization initiator in this invention, it may be used in combination with a reducing agent to effect the reaction in the form of redox polymerization. As concrete examples of the reducing agent used for this purpose, (hydrogen) sulfites such as sodium sulfite and sodium hydrogen sulfite; thiosulfates such as sodium thiosulfate; dithionites; metal salts such as cuprous sulfate and ferrous sulfate; organic reducing agents such as L-ascorbic acid; and amines such as aniline and monoethanol amine may be cited.

The radical polymerization initiator may be added all at once or gradually added to the polymerization system. The amount of the radical polymerization initiator to be used is generally in the range of 0.001 to 2 mol %, preferably 0.01 to 1 mol %, based on the amount of the water-soluble unsaturated monomer.

The radical polymerization for the production of the acrylate polymer may be performed by any of the known techniques. As typical examples of the method of radical polymerization, various forms of aqueous solution polymerization such as cast polymerization performed in a molding frame (JP-B-48-42,466), polymerization to be performed on a belt conveyor (JP-A-58-49,714), polymerization performed on a finely divided hydrogel polymer (JP-A-57-34, 101, U.S. Pat. No. 4,625,001 and U.S. Pat. No. 5,124,416), and polymerization performed under pressure (JP-A-2-129, 207), reversed-phase suspension polymerization (JP-B-59-37,003), reversed-phase emulsion polymerization (JP-A-63-90,510 and JP-A-63-90,537), polymerization of a monomer complexed with a fibrous substrate (JP-A-2-242,975), precipitation polymerization (JP-A-58-84,819, JP-A-1-1,710, and JP-A-1-204,910), and bulk polymerization may be cited.

When the water-soluble unsaturated monomer is polymerized in the form of a solution, the acrylate polymer resulting from the polymerization may be put to use in its unmodified form. However, it is, preferably used in a dried form for the purpose of enhancing its convenience of handling and decreasing the residual monomer content.

The drying of the acrylate polymer in this invention may be carried out by any of the methods of drying known to the art. For example, a method which comprises polymerizing a monomer at a high concentration thereby simultaneously effecting the drying and polymerization by virtue of the heat of polymerization (JP-A-58-71,907 and JP-A-2-34,607) may be adopted. The produced gel polymer may be further dried, depending on the solids content of the produced polymer.

The methods which maybe effectively used for the further drying of the gel polymer include, for example, drying under conditions of high humidity (JP-A-1-26,604), azeotropic dehydration in an organic solvent, drying by means of microwave, drying using a belt or a drum drier heated to a prescribed temperature, drying in a cylinder furnished with a high-speed rotor (JP-A-2-240,112), and drying by the use of a forced draft oven, an infrared ray, or a vacuum drying device.

The temperature for drying the gel polymer in this invention is generally in the range of 70° to 300° C., preferably 110° to 260° C., and more preferably 150° to 250° C. If this temperature is less than 70° C, the drying takes an unduly long time. If the temperature exceeds this range, decreasing effect of the residual monomer by using the momers in accordance of the present invention is difficult to occur. Particularly when the acrylate polymer is an absorbent resin, the drying performed at a temperature in the range of 110° to 260° C., preferably 150° to 250° C. is preferred in that not only the reduction of residual monomer but also the absorption ratio is enhanced. The time for the drying operation is suitably decided by the water content and the particle diameter of the gel polymer and the temperature of drying. It is generally in the range of one minute to 10 hours, preferably 10 minutes to five hours.

The drying performed at an elevated temperature has been heretofore found to be preferable from the standpoint of operational efficiency. However, it necessarily involves an increase in the residual monomer content. In the process of searching for the cause of this inevitable increase in the residual monomer content, we have found this increase in the residual monomer content occurs while the drying is in process. Thus, the problem of the increase in the residual monomer content has been solved. To be specific, the use of the water-soluble unsaturated monomer according to this invention enables an acrylate polymer having only a small residual monomer content and excellent physical properties such as excellent absorption capacity to be obtained without reference to the temperature of drying and the time for drying.

Further, ammonia is used for neutralization, it is preferred that the polymer is subjected to heat treatment in order to decrease the residual monomer content.

The state to be assumed by the polymer prior to heat treatment is not particularly discriminated by this invention. For example, the polymer may be in the form of a gel fresh from polymerization, a dispersion in an organic solvent, or a dry solid. The solids content of the polymer prior to heat treatment may be kept at a constant level or may be increased by vaporizing the solvent. For example, specifically, in regard to the timing for carrying out the heat treatment, the step of drying, the step of surface cross-linking, the step of reheating after drying, the step of pelletizing, and the step of using additives may be cited. The heat treatment which is performed at the step of drying at the above mentioned temperature proves to be particularly preferred. Specifically if the gel polymer of this invention is an absorbent resin, the enhancement of the absorption ratio and the notable decrease of the residual monomer content are accomplished by drying the gel polymer at the temperature mentioned above and subjecting it to heat treatment. The method adopted for the drying is not particularly discriminated by this invention. Such known methods of drying as hot air drying, infrared ray drying, and azeotropic dehydration are concrete examples. Further, when ammonia is used together, ammonia used for neutralization apt to volatile at heat treatment, it is necessary to pay attention to odor during a process and control of properties of the polymer along with decrease of neutralization ratio.

The absorbent resin freshly polymerized or dried may incorporate therein such additives as a surfactant, an inorganic fine powder, and a (hydrogen) sulfite. It may be otherwise pulverized or pelletized for the purpose of adjustment of particle size. When a powder absorbent resin is to be obtained, the absorbent resin particle size is adjusted to an average particle diameter in the range of 10 to 1,000 µm, more preferably 100 to 1,000 µm, and most preferably 300 to 600 µm.

The acrylate polymer having a cross-linked surface region which is provided by this invention can be obtained by cross-linking the surface region of the acrylate polymer which has been produced by the method described above.

When the acrylate polymer which is obtained from a water-soluble unsaturated monomer having a β-hydroxy propionic acid content of not less than 1,000 ppm is used as the acrylate polymer intended to be furnished with a cross-linked surface region, the surface cross-linking induces an increase in the residual monomer content and exerts an adverse effect on the safety of the product.

As respects the water content of the acrylate polymer used in this invention, though the acrylate polymer resulting from the polymerization may be put to use in its undried form, it is generally preferred to use the acrylate polymer in its dried form from the standpoint of the effect of the surface cross-linking. To be specific, the acrylate polymer which has a cross-linked surface region is preferably dried until the water content thereof falls below 40%, preferably below 30%, and more desirably below 10%.

Regarding the particle size of the acrylate polymer to be used in this invention, preferably the average particle diameter is in the approximate range of 10 to 2,000 µm, more preferably 100 to 1,000 µm, and most preferably 300 to 600 µm. The particle size distribution of this acrylate polymer is preferred to be as narrow as possible.

The acrylate polymer used herein may be a water-soluble resin. The effect of the surface cross-linking of this invention brought about in improving various physical properties of the polymer is produced more noticeably in the acrylate polymer in the form of an absorbent resin.

The second cross-linking agent used for cross-linking the surface region of the acrylate polymer in this invention may be any of the known cross-linking agents which generally find extensive utility in numerous applications. As concrete examples of the second cross-linking agent, polyhydric alcohols, polyepoxy compounds, polyamines, polyaziridines, polyaldehydes, polyisocyanates, polyoxazolines, alkylene carbonates, and polyvalent metals may be cited. The compounds which have such functional groups are other examples.

The polyhydric alcohols which may be effectively used include, for example, ethylene glycol, diethylene glycol, propylene alcohol, triethylene glycol, tetraethylene glycol, polyethylene glycol, propylene glycol, 1,3-propane diol, dipropylene glycol, 2,2,4-trimethyl-1,3-pentadiol, polypropylene glycol, glycerol, polyglycerol, 2-butene-1,4-diol, 1,4-butane diol, 1,5-pentane diol, 1,6-hexane diol, 1,2-cyclohexane dimethanol, 1,2-cyclohexanol, trimethylol propane, diethanol amine, triethanol amine, polyoxy propylene, oxyethylene-oxypropylene block copolymer, pentaerythritol, and sorbitol.

The polyepoxy compounds which may be effectively used include, for example, ethylene glycol diglycidyl ether, diglycerol polyglycidyl ether, polyglycerol polyglycidyl ether, propylene glycol diglycidyl ether, and polypropylene glycol diglycidyl ether.

The polyamines which may be effectively used include, for example, ethylene diamine, diethylene triamine, triethylene tetramine, tetraethylene pentamine, pentaethylene hexamine, and polyethylene imine.

The polyaziridines which may be effectively used include, for example, 2,2-bis-hydroxymethyl butanol tris(3-(1-aziridinyl)propionate), 1,6-hexanemethylene diethylene urea, and diphenyl-methane-bis-4,4-N,N'-diethylene urea.

The polyaldehydes which may be effectively used include, for example, glyoxal and glutar aldehyde.

The polyisocyanates which may be effectively used include, for example, 2,4-tolylene diisocyanate and hexamethylene diisocyanate.

The polyoxazolines which may be effectively used include, for example, 1,2-ethylene bis oxazoline and polyisopropenyl oxazoline, for example.

The alkylene carbonates which may be effectively used include, for example, 1,3-dioxolan-2-on, 4-methyl-1,3-dioxolan-2-on, 4,5-dimethyl-1,3-dioxolan-2-on, 4,4-dimethyl-1,3-dioxolan-2-on, 4-ethyl-1,3-dioxolan-2-on, 4-hydroxymethyl-1,3-dioxolan-2-on, 1,3-dioxan-2-on, 4-methyl-1,3-dioxan-2-on, 4,6-dimethyl-1,3-dioxane-2-on, and 1,3-dioxoban-2-on.

The haloepoxy compounds which may be effectively used include, for example, epichlorohydrin, epibromohydrin, and α-methyl epichlorohydrin.

The polyvalent metals which may be effectively used as a surface cross-linking agent herein include, for example, hydroxides and chlorides of zinc, calcium, magnesium, aluminum, iron, and zirconium.

As the cross-linking agent for use in this invention, it is preferable to adopt one member or a combination of two or more members selected from the group of cross-linking agents mentioned above. In the light of the effect of surface cross-linking, it is preferable to use as the cross-linking agent one member or a combination of two or more members selected from the group consisting of polyhydric alcohols, polyglycidyl compounds, poly-amines, and alkylene carbonates. Particularly from the viewpoint of not only the effect of surface cross-linking but also the safety and cost, it is most preferable to use a polyhydric alcohol as the surface cross-linking agent.

The amount of the surface cross-linking agent to be used in this invention, although variable with the type of cross-linking agent used, is generally in the range of 0.001 to 20 parts by weight, preferably 0.01 to 10 parts by weight, based on 100 parts by weight of the solids of the acrylate polymer obtained by this invention. So long as this amount is in the range just mentioned, the acrylate polymer having a cross-linked surface region can be obtained with excellent physical properties. If the amount of the surface cross-linking agent to be used exceeds 20 parts by weight, the excess not merely impairs the economics of the production but also constitutes in itself an extravagance for accomplishing the proper effect of cross-linking. If this amount is so small as to fall short of 0.001 part by weight, the surface cross-linking does not easily bring about an improvement of the various physical properties.

In this invention, water may be used in mixing the acrylate polymer with the cross-linking agent. In this invention, the amount of water to be used is not more than 20 parts by weight, preferably in the range of 0.5 to 10 parts by weight, based on 100 parts by weight of the solids of the acrylate polymer, depending on the type, particle size, and water content of the acrylate polymer.

In this invention, a hydrophilic organic solvent may be used in mixing the cross-linking agent and the acrylate polymer. The hydrophilic organic solvents which may be effectively used include, for example, lower alcohols such as methyl alcohol, ethyl alcohol, n-propyl alcohol, isopropyl alcohol, n-butyl alcohol, isobutyl alcohol, and t-butyl alcohol; ketones such as acetone; ethers such as dioxane and tetrahydrofuran; amides such as N,N-dimethyl formamide; and sulfoxides such as dimethyl sulfoxide. Though the optimum amount of the hydrophilic organic solvent used in this invention varies with the type and particle size of the acrylate polymer, it is generally in the range of 0 to 10 parts by weight, preferably 0 to 8 parts by weight, based on 100 parts by weight of the solids of the acrylate polymer.

In this invention, the acrylate polymer and the cross-linking agent (and water/hydrophilic organic solvent) may be mixed either in a non-dispersed system or in a dispersed system.

The mixture of the acrylate polymer with the cross-linking agent in the non-dispersed system is effected, for example, by such a method as disclosed in DE-A-4020780. This method comprises directly spraying the cross-linking agent or the mixed liquid of the cross-linking agent and water and/or a hydrophilic organic solvent onto the acrylate polymer or adding it dropwise thereto. When water is used in the mixture effected in the non-dispersed system, the mixing may be performed in the presence of an inorganic compound or incorporating a surfactant for the purpose of ensuring uniform dispersion of the cross-linking agent in the produced mixture (U.S. Pat. No. 4,587,308 and EP-A-0509706). Optionally, the incorporation of water in the process of mixing may be carried out in the form of steam (JP-A-1-297,430).

As concrete examples of the method for mixing the acrylate polymer with the cross-linking agent in the dispersed system, a method which comprises dispersing the acrylate polymer in a hydrophilic organic solvent (JP-A-57-44,627) and a method which comprises dispersing the acrylate polymer in a hydrophobic solvent (JP-A-59-62,665) may be cited. The surface cross-linking treatment in the dispersed system is also preferably carried out in the presence of a prescribed amount of water (JP-A-58-117,222).

After the acrylate polymer has been mixed with the cross-linking agent in the non-dispersed system or dispersed system, the resultant mixture is further heated to have the surface region thereof cross-linked, depending on the type of cross-linking agent. Generally, it is desirable to heat-treat this mixture for the purpose of promoting the cross-linking reaction and, at the same time, volatilizing the organic solvent and water which have been added optionally in the process of the mixing.

As concrete examples of the method for performing this heat treatment, a method which comprises directly heating the acrylate polymer which has a surface cross-linking agent incorporated therein in the non-dispersed system, a method which comprises subjecting the acrylate polymer having a cross-linking agent incorporated therein to a heat treatment per se in the dispersed system, and a method which comprises removing the acrylate polymer by filtration from the dispersed system and heat-treating the separated acrylate polymer in the non-dispersed system may be cited.

In this invention, when the heat treatment is carried out after the addition of the cross-linking agent, the temperature of this heat treatment is generally not less than 75° C., preferably in the range of 100° C. to 300° C., more preferably 120° to 260° C., and most preferably 150° to 250° C. If the temperature of this heat treatment is unduly low, decreasing effect of the residual monomer by using the monomers in accordance with the present invention is difficult to occur, and the heat treatment takes an excessively long time and the operational efficiency of heat treatment is degraded and uniform and fast surface cross-linking cannot be easily attained. Conversely, if the temperature is so high as to exceed 300° C., the acrylate polymer maybe subject to thermal deterioration. The duration of the heat treatment is suitably decided with due consideration to the desired effect of the surface treatment and the temperature of heat treatment.

Heretofore, the practice of performing the heat treatment at a high temperature, for example, falling in the range of 120° to 260° C. has been advocated for the purpose of allowing the surface cross-linking to proceed uniformly and quickly. We have found that the heat treatment performed at this elevated temperature increases the residual monomer content in the acrylate polymer to a level in the range of some tens to some thousands of ppm. The acrylate polymer according to the present invention, however, shows virtually no increase in the residual monomer content during the heat treatment of the surface cross-link irrespective of the temperature of heating or the duration of heating. And when the polymer is neutralized using ammonia, the residual monomer content rather decreases. The conventional heat treatment has failed to effect sufficient improvement in the various physical properties of the polymer perhaps because of the generation and growth of residual monomer in the polymer during the surface treatment.

So long as the acrylate polymer described above is adopted, the treatment with a surface cross-linking agent and the heat treatment enable the acrylate polymer to acquire an improved quality and form a cross-linked texture in the surface region thereof and allows virtually no increase in the residual monomer content irrespective of the method adopted for the addition of the surface cross-linking agent or the method of heat treatment. Since the addition of the cross-linking agent in the dispersed system and the heat treatment in the dispersed system require a large amount of organic solvent, the heat treatment is preferably carried out in the non-dispersed system from for the benefit of the operational efficiency and the safety of the heat treatment. Further from the standpoint of the quality of the produced resin, not only the heat treatment but also the addition of the surface cross-linking agent is preferably carried out in the non-dispersed system.

Further the absorbent resin in accordance with the present invention has not more than 100 ppm, preferably not more than 10 ppm of residual monomer content in substantial dry state and is an absorbent resin which contains acrylic acid (salt) containing not more than 100 ppm, preferably not more than 10 ppm of residual monomer content after heating at a temperature of 180° C. for 3 hours.

In a conventional absorbent resin, the residual monomer content is merely decreased apparently, but a large amount of residual monomer generates by heating. However, the absorbent resin in accordance with the present invention has a residual monomer content of not more than 100 ppm, ever after heating at a temperature of 180° C. for 3 hours and the residual monomer content sometime rather decreases and safe under any condition. This is based on the reason that the acrylic acid salt polymer in accordance with the present invention is a novel acrylic acid salt polymer composition in which β-hydroxy propionic acid content is extremely decreased, for example, 1 to 1000 ppm, preferably 1–500 ppm, more preferably 1 to 100 ppm compared to a conventional polymer.

Now, this invention will be described more specifically below with reference to the working examples. It should be noted, however, that the scope of this invention is not limited to these working examples in any respect. The physical properties of the acrylate polymer which will be described in these working examples represents the magnitudes determined by the following testing methods.

The term "latent residual monomer content" as used herein refers to the residual monomer which occurs as an increment produced by protracted use of the polymer or exposure of the polymer to an elevated temperature to the residual monomer generally found in the acrylate polymer at normal room temperature. Of course, a the latent residual monomer content is large notwithstanding the fact that the apparent residual monomer content is small is undesirable from the standpoint of safety.

(1) Absorption Capacity

This property is determined by placing 0.2 g of a given acrylate polymer uniformly in a teabag-like pouch (40×150 mm) made of non-woven fabric, keeping the pouch containing the sample immersed in an aqueous 0.9 wt % sodium chloride solution for 30 minutes, removing the pouch from the solution, allowing the drenched pouch to drain for a prescribed time, weighing the wet pouch, and calculating the following formula using the weight.

Absorption ratio (g/g)=((Weight of wet pouch)−(Weight of wet blank pouch))/(Weight of absorbent resin)

(2) Residual Monomer Content

This magnitude is determined by stirring a dispersion of 0.5 g of a given acrylate monomer in 1,000 ml of deionized water for two hours, passing the resultant dispersion through a Wattman filter paper, and assaying the filtrate for residual monomer content by means of high-speed liquid chromatography.

(3) Latent Residual Monomer Content

A given acrylate polymer is heated at 180° C. for three hours to facilitate analysis thereof for the latent residual acrylic acid content. The acrylate polymer which has undergone this heat treatment is tested for the residual monomer content by the method of (2) above. The increasement produced in the residual monomer content as a consequence of the heat treatment is reported as the latent residual monomer content.

(4) Suction Power

This property is determined by preparing a petri dish having the inner bottom thereof covered with tissue paper, pouring 20 ml of artificial urine (containing 1.9% of urea, 0.8% of NaCl, 0.1% of $CaCl_2$, and 0.1% of $MgSO_4$) into the petri dish, dropping 1 g of a given acrylate polymer having a cross-linked surface region at the center of the petri dish, allowing the sample to absorb the artificial urine through the tissue paper for 10 minutes, weighing the swollen gel, and determining the increase in the weight of the sample. This increase is reported as the magnitude of the suction power of the sample.

Acrylate to be Used

The acrylates used in the following working examples and controls were products obtained by the following procedure. The contents of β-hydroxy propionic acid in the produced acrylates and the polymers were magnitudes expressed in ppm, based on the solids determined by liquid chromatography.

The species of acrylic acid refined by distillation were stored in a dark room at a fixed temperature in the range of 200 to 40° C. (assuming a normal room temperature) until they were in the neutralization step. As things stand, some tens of days elapse before the acrylic acid refined by distillation at production facilities reaches the end consumer engaging in the production of the hydrophilic resin. More often than not, the acrylic acid is handled in an about 80% aqueous solution having a high point of solidification so as to prevent it from freezing.

Production 1

Acrylic acid obtained from an acrylic acid production plant was refined by distillation. The refined acrylic acid was stored at 30° C. for 3 hours and then neutralized by the following procedure of Example 1 cited in EP-A-0372706.

A distillation flask provided with a stirrer was charged with 2,744 g of deionized water. With the temperature of the neutralization reaction system inside the flask kept at a level in the range of 20° to 40° C., 1,390 g of the acrylic acid and 1,480 g of an aqueous 48 wt % sodium hydroxide solution were simultaneously added dropwise over a period of 100 minutes into the flask at a sodium hydroxide/acrylic acid dropping ratio in the range of 0.9 to 0.95. After the end of the dropwise addition, 160 g of an aqueous 48 wt % sodium hydroxide solution was supplied to the flask to adjust the ratio of neutralization of the neutralization reaction system inside the flask to 102 mol %. With the temperature of the neutralizing reaction system adjusted to 40° C., the product of neutralization was left aging for 30 minutes. Subsequent to the completion of the aging, 499 g of acrylic acid was supplied over a period of 10 minutes to the neutralization reaction system to obtain an acrylate (I) of a concentration of 37% with a ratio of neutralization of 75 mol %.

The content of β-hydroxy propionic acid in the acrylate (I) was found to be 40 ppm based on the solids of the acrylate.

Productions 2 and 3

Acrylates (II) and (III) were obtained by following the procedure of Production 1, except that samples of acrylic acid which had been stored at a temperature of 30° C. for 10 hours and 24 hours respectively after the refinement by distillation were used for the neutralization.

The contents of β-hydroxy propionic acid in the acrylates (II) and (III) based on the solids thereof were found to be 90 ppm and 190 ppm respectively.

Production 4

An acrylate (IV) was obtained by following the procedure of Production 1, except that a sample of acrylic acid which had been stored at a temperature of 25° C. for 24 hours after being refined by distillation was used for the neutralization. The content of β-hydroxy propionic acid in the acrylate (IV) based on the solids thereof was found to be 100 ppm.

Productions 5 to 7

Acrylates (V) to (VII) were obtained by following the procedure of Production 1, except that samples of acrylic acid which had been stored at a temperature of 20° C. for 10 hours, 24 hours, and 48 hours respectively after being refined by distillation were used for the neutralization. The contents of β-hydroxy propionic acid in the acrylates (V) to (VII) based on the solids thereof were found to be 50 ppm, 80 ppm, and 130 ppm respectively.

Production 8

A commercially available acrylic acid (guaranteed reagent produced by Wako Junyaku K.K.) was refined by distillation. The refined acrylic acid was stored at a temperature of 30° C. for 3 hours and then neutralized by the following procedure of Control 2 cited in EP-A-0372706.

A distillation flask provided with a stirrer was charged with 2,744 g of deionized water and 1,640 g of an aqueous 48 wt % sodium hydroxide solution. Then, with the temperature of the neutralization reaction system kept at a level in the range of 20° to 40° C., 1,889 g of the acrylic acid was supplied over a period of 120 minutes to the flask to obtain an acrylate (VIII) of a concentration of 37% at a ratio of neutralization of 75 mol %. The content of β-hydroxy propionic acid in the acrylate (VIII) based on the solids thereof was found to be 230 ppm.

Productions 9 and 10

Acrylates (IX) and (X) were obtained by following the procedure of Production 8, except that samples of acrylic acid which had been stored at a temperature of 30° C. for 10 hours and 24 hours respectively after the refinement by distillation were used for the neutralization. The contents of β-hydroxy propionic acid in the acrylates (IX) and (X) based on the solids thereof were found respectively to be 290 ppm and 390 ppm.

Production 11

A commercially available acrylic acid (guaranteed reagent produced by Wako Junyaku K.K.) was refined by distilla-tion. The refined acrylic acid was converted into an aqueous 80% solution having a high point of solidification there by allowing easy handling. The aqueous solution was stored at a temperature of 30° C. for three hours and then neutralized by the following procedure resembling that of Production 8.

A distillation flask provided with a stirrer was charged with 2,272 g of deionized water and 1,640 g of an aqueous 48 wt % sodium hydroxide solution. Then, with the temperature of the neutralization reaction system kept at a level in the range of 200 to 40° C., 2,361 g of an aqueous 80% acrylic acid solution was supplied over a period of 120 minutes to the flask to obtain an acrylate of a concentration of 37% with a ratio of neutralization of 75 mol %.

The content of β-hydroxy propionic acid in the acrylate (XI) based on the solids thereof was found to be 290 ppm.

Production 12

An acrylate (XII) was obtained by effecting neutralization in accordance with the procedure of Production 8, except that the temperature of neutralization was lowered to 10° C. However, due to the fall of the temperature of neutralization, the time required for the neutralization increased to six hours, a period three times the period required in Example 8 of Production. The content of β-hydroxy propionic acid in the acrylate (XII) based on the solids thereof was found to be 70 ppm.

Production 13

An acrylate (XIII) of a concentration of 45% having a ratio of neutralization of 50 mol % was obtained by following the procedure of Production 1, except that the amount of the acrylic acid added to the neutralization reaction system subsequent to the completion of the aging at a ratio of neutralization of 102 mol % was changed from 499 g to 1,446 g. The content of β-hydroxy propionic acid in the acrylate (XIII) based on the solids thereof was found to be 30 ppm.

Production 14

An acrylate (XIV) of a concentration of 34% having a ratio of neutralization of 90 mol % was obtained by following the procedure of Production 1, except that the amount of acrylic acid added to the neutralization reaction system subsequent to the completion of the aging at a ratio of neutralization of 102 mol % was changed from 499 g to 184 g. The content of β-hydroxy propionic acid in the acrylate (XIII) based on the solids thereof was found to be 50 ppm.

Production 15

An acrylate (XV) of a concentration of 37% having a ratio of neutralization of 100 mol % was obtained by following the procedure of Production 8, except that the amount of the deionized water was changed from 2,744 g of 1,942 g and the amount of acrylic acid added dropwise to the neutralization reaction system was changed from 1,889 g to 1,418 g. The content of β-hydroxy propionic acid in the acrylate (XV) based on the solids thereof was found to be 290 ppm.

Control Production 1

An acrylate (I) for comparison was obtained by following the procedure of Production 1, except that acrylic acid stored at 25° C. for 20 days after being refined by distillation was used instead for the neutralization. The content of β-hydroxy propionic acid in the acrylate (I) for comparison based on the solids thereof was found to be 2,500 ppm.

Control Production 2

An acrylate (II) for comparison was obtained by following the procedure of Production 1, except that a commercially available acrylic acid (guaranteed reagent produced by Kanto Kagaku K.K.) was used for neutralization without being refined in advance by distillation. The content of β-hydroxy propionic acid in the acrylate (II) for comparison based on the solids thereof was found to be 4,200 ppm.

Production 3

An acrylate (III) for comparison was obtained by following the procedure of Production 1, except that a commercially available acrylic acid (guaranteed reagent produced by Wako Junyaku K.K.) was used for neutralization without being refined in advance by distillation. The content of β-hydroxy propionic acid in the acrylate (III) for comparison based on the solids thereof was found to be 8,200 ppm.

Control Productions 4 and 5

Acrylates (IV) and (V) for comparison were obtained by following the procedure of Production 1, except that samples of acrylic acid which had been stored respectively for 120 hours and 240 hours after the refinement by distillation were used instead for neutralization. The contents of β-hydroxy propionic acid in the acrylates (IV) and (V) for comparison based on the solids thereof were found to be respectively 1,100 ppm and 1,900 ppm.

Control Production 6

An acrylate (VI) for comparison was obtained by following the procedure of Production 1, except that acrylic acid which had been stored at a temperature of 40° C. for 48 hours after the refinement by distillation was used instead for neutralization. The content of β-hydroxy propionic acid in the acrylate (VI) for comparison based on the solids thereof was found to be 1300 ppm.

Control Productions 7 and 8

Acrylates (VII) and (VIII) for comparison were obtained by following the procedure of Production 8, except that samples of acrylic acid which had been stored respectively for 120 hours and 240 hours after the refinement by distillation were used instead for neutralization. The contents of β-hydroxy propionic acid in the acrylates (VII) and (VIII) for comparison based on the solids thereof were found to be respectively 1,300 ppm and 2,100 ppm.

Control Productions 9 and 10

Acrylates (IX) and (X) for comparison were obtained by following the procedure of Production 11, except that aqueous acrylic acid solutions which had been stored for 240 hours and 480 hours respectively after the refinement by distillation were used instead for neutralization. The contents of β-hydroxy propionic acid in the acrylates (IX) and (X) based on the solids thereof were found to be respectively 3,300 ppm and 6,700 ppm.

Control Production 11

When the procedure of Production 8 was repeated, except that the temperature of the neutralization system was elevated from a level in the range of 20° to 40° C. to a level in the range of 50° to 60° C. for the purpose of decreasing the time required for neutralization, the time of neutralization was decreased from 120 minutes to 40 minutes. The content of β-hydroxy propionic acid in the resultant acrylate was 2,100 ppm. Hereinafter, this acrylate will be referred to as "acrylate (XI) for comparison."

Control Production 12

An acrylate (XII) for comparison having a β-hydroxy propionic acid content of 1,800 ppm and a ratio of neutralization of 50 mol % was obtained by following the procedure of Production 13, except that the same acrylic acid as used in Control Production 1 was used for neutralization.

Control Production 13

An acrylate (XIII) for comparison having a β-hydroxy propionic acid content of 3,200 ppm and a ratio of neutralization of 100 mol % was obtained by following the procedure of Production 15, except that the same acrylic acid as used in Control Production 1 was used for neutralization.

EXAMPLE 1

A water-soluble unsaturated monomer (I) (concentration 37% and ratio of neutralization 75 mol %) having a β-hydroxy propionic acid content of 40 ppm was obtained by dissolving 1.8 g of N,N'-methylene bis-acrylamide as a cross-linking agent in 5,500 g of the acrylate (I) obtained in Production 1.

The water-soluble unsaturated monomer deaerated with nitrogen gas for 30 minutes was supplied to a reaction vessel constructed by fitting a lid on a jacketed twin-arm type kneader of stainless steel having an inner volume of 10 liters and provided with two sigma type vanes. With the water-soluble unsaturated monomer (I) kept at a constant temperature of 30° C., the entrapped gas in the reaction system was displaced with nitrogen. Then, the reaction vessel was kept heated by passing hot water at 35° C. through the jacket and in the meanwhile 0.3 mol % of ammonium persulfate and 0.03 mol % of sodium hydrogen sulfite were added to the reaction vessel. Two hours had elapsed between the time the water-soluble unsaturated monomer (I) was prepared by the procedure described above and the time polymerization of this monomer was initiated by the addition of an initiator.

The polymerization was initiated one minute after the addition of the initiator. The peak temperature in the reaction system reached 83° C. after 16 minutes thence. At this time, the resultant hydrogel polymer was divided into particles about 5 mm in diameter. The stirring of the interior was further continued. After 60 minutes following the start of polymerization, the hydrogel polymer was removed from the reaction vessel. The minute particles of the hydrogel polymer thus obtained were spread on a metallic net of 50 mesh and dried with hot air thereon at 130° C. for 90 minutes. The dried particles were pulverized by the use of a vibration mill and further classified with a 20-mesh screen to obtain an absorbent resin of acrylate (1). The absorbent resin of acrylate (1) was tested for residual monomer content, latent residual monomer content, and absorption ratio. The results are shown in Table 1.

EXAMPLES 2 TO 4

Absorbent resins of acrylate (2) to (4) were obtained by repeating the procedure of Example 1, except that the time between the preparation of the water-soluble unsaturated monomer (I) and the start of polymerization was increased to 6 hours, 12 hours, and 24 hours respectively by standing for necessary time. The physical properties of these absorbent resins are shown in Table 1.

EXAMPLES 5 TO 7

Water-soluble unsaturated monomers (II) to (IV) having β-hydroxy propionic acid contents of 90 ppm, 190 ppm, and 100 ppm respectively were obtained by repeating the procedure of Example 1, except that the acrylates (II) to (IV) were used in the place of the acrylate (I).

By setting the water-soluble unsaturated monomers (II) to (IV) undergoing polymerization in the same manner as in Example 1, 2 hours after their preparation, absorbent resins of acrylate (5) to (7) were obtained. The physical properties of these absorbent resins are shown in Table 1.

EXAMPLE 8

A water-soluble unsaturated monomer (V) having a β-hydroxy propionic acid content of 50 ppm was obtained by repeating the procedure of Example 1, except that the acrylate (V) was used instead of acrylate (I) in the preparation of water-soluble unsaturated monomer and 2.2 g of polyethylene glycol diacrylate (0.02 mol % based on the monomer) (average n number 8) was used in the place of the N,N'-methylene bis-acrylamide as the cross-linking agent.

The water-soluble unsaturated monomer (V) was polymerized in the same manner as in Example 1, 6 hours after preparation. The gel polymer thus obtained was dried at 150° C. for 75 minutes and then pulverized and classified in the same manner as in Example 1 to obtain an absorbent resin of acrylate (8). The physical properties of the absorbent resin are shown in Table 1.

EXAMPLES 9 AND 10

Water-soluble unsaturated monomers (VI) and (VII) having β-hydroxy propionic acid contents of 80 ppm and 130 ppm respectively were obtained by following the procedure of Example 8, except that the acrylates (VI) and (VII) were used instead acrylate (V) in the preparation of the water-soluble unsaturated monomer.

Then, the water-soluble unsaturated monomers (VI) and (VII) were treated in the same manner as in Example 8 to obtain absorbent resins of acrylate (9) and (10). The physical properties of these absorbent resins are shown in Table 1.

EXAMPLE 11

A water-soluble unsaturated monomer (VIII) having a β-hydroxy propionic acid content of 230 ppm was obtained by following the procedure of Example 1, except that the acrylate (VIII) was used instead of the acrylate (I) in the preparation of the water-soluble unsaturated monomer and 13.6 g of trimethylol propane triacrylate (0.2 mol % based on the monomer) was used instead of the N,N'-methylene bis-acrylamide as the cross-linking agent.

The water-soluble unsaturated monomer (VIII) was polymerized in the same manner as in Example 1, 2 hours after the preparation thereof. The gel-polymer consequently obtained was dried at 180° C. for 60 minutes and then treated in the same manner as in Example 1 to obtain an absorbent resin of acrylate (11). The physical properties of this resin are shown in Table 1.

EXAMPLES 12 AND 13

Water-soluble unsaturated monomers (IX) and (X) having β-hydroxy propionic acid contents of 290 ppm and 390 ppm respec-tively were obtained by following the procedure of Example 11, except that the acrylates (IX) and (X) were used instead of acrylate (VIII) in the preparation of water-soluble unsaturated monomer.

Then, the water-soluble unsaturated monomers (IX) and (X) were treated in the same manner as in Example 11 to obtain absorbent resins of acrylate (12) and (13). The physical properties of these absorbent resins are shown in Table 1.

EXAMPLE 14

In a reaction vessel provided with a stirrer, a nitrogen inlet tube, and a thermometer, a water-soluble unsaturated monomer (XI) having a β-hydroxy propionic acid content of 230 ppm was prepared by dissolving 30 g of corn starch in 600 g of water and further dissolving 718 g (3 mols) of the acrylate (XI), 71 g (1 mol) of acrylamide, and 0.12 g (0.01 mol % based on the monomer) of trimethylol propane triacrylate in the aqueous starch solution.

The water-soluble unsaturated monomer (XI) was left standing at 30° C. for two hours. Then, it was blown with a forced current of nitrogen gas for one hour to expel the dissolved oxygen. This water-soluble unsaturated monomer was combined with 0.1 mol % of sodium persulfate as a polymerization catalyst and 0.05 mol % of l-ascorbic acid and the resultant hydrogel was polymerized for 3 hours. Further, this hydrogel was dried in the form of a thick film by the use of a double drum drier having a surface temperature of 150° C. The dry film was pulverized and classified with a 20-mesh screen to obtain an absorbent resin of acrylate (14). The results of the analysis of this absorbent resin are shown in Table 1.

EXAMPLE 15

A water-soluble unsaturated monomer (XII) having a β-hydroxy propionic acid content of 70 ppm was obtained by dissolving 3.4 g (0.1 mol % based on the monomer) of tetraethylene glycol diacrylate in 1,000 g of acrylate (XII).

The water-soluble unsaturated monomer (XII) freshly prepared was left standing at 50° C. and blown with a forced current of nitrogen gas to expel the dissolved oxygen. Then, the monomer was spread in the form of a layer, 5 mm in thickness under an atmosphere of nitrogen and was polymerized thereon by having 0.2 mol % of 2,2'-azo-bis(2-amidinopropane)dihydrochloride sprayed thereon. Two hours had elapsed between the time the water-soluble unsaturated monomer was prepared and the time the polymerization thereof was initiated.

The polymerization was immediately initiated. The gel polymer consequently formed was removed from the reaction vessel after 10 minutes of the polymerization. It was pulverized and dried with hot air at 150° C. for 60 minutes. The dry gel polymer was pulverized and classified in the same manner as in Example 1 to obtain an absorbent resin of acrylate (15). The results of the analysis of the absorbent resin are shown in Table 1.

EXAMPLES 16 AND 17

Absorbent resins of acrylate (16) and (17) were obtained by following the procedure of Example 15, except that the water-soluble unsaturated monomer (XII) was left standing and polymerizing at 30° C. for 12 hours and 24 hours respectively after preparation until polymerization. The results of the analysis of these absorbent resins are shown in Table 1.

EXAMPLE 18

A water-soluble unsaturated monomer of a concentration of 35% having a ratio of neutralization of 75% and a β-hydroxy propionic acid content of 70 ppm was prepared by using 83.4 g of the acrylate (XII), 0.004 g of N,N'-methylene bis-acrylamide (0.0065 mol % based on the monomer) as a cross-linking agent, and 17.77 g of deionized water. Three hours after the completion of preparation, the water-soluble unsaturated monomer was blown with a forced current of nitrogen gas to expel the dissolved oxygen.

Separately, in a four-neck separable flask having an inner volume of 500 ml and provided with a stirrer, a reflux condenser, a thermometer, a nitrogen gas inlet tube, and a dropping funnel, 250 ml of cyclohexane was placed, 2.0 g of sorbitan monostearate (HLB 4.7) as a dispersant was dissolved in the cyclohexane, and the resultant solution was blown with a forced current of nitrogen gas to expel the dissolved oxygen.

The water-soluble unsaturated monomer was deaerated for one hour and 0.06 mol % of potassium persulfate was dissolved in the monomer. The resultant solution was placed in the separable flask mentioned above and stirred to effect dispersion therein at a rate of 250 rpm. Then, the resultant mixture was heated to 60° C. to initiate a polymerization reaction. (Incidentally, four hours had elapsed between the time the water-soluble unsaturated monomer was prepared and the time polymerization was initiated.)

After the start of polymerization, the polymerization mixture was kept at the temperature mentioned above for two hours and subsequently subjected to azeotropic dehydration. When the water content of the resultant polymer fell below 10%, the polymer was separated by filtration and dried in an oven at 130° C. for 1 hour to obtain an absorbent resin of acrylate (18). The physical properties of this resin are shown in Table 1.

EXAMPLE 19

A water-soluble unsaturated monomer (XIII) of a concentration of 45% having a β-hydroxy propionic acid of 30 ppm and a ratio of neutralization of 50% was obtained by following the procedure of Example 1, except that the acrylate (XIII) was used instead of the acrylate (I) in the preparation of water-soluble unsaturated monomer.

The water-soluble unsaturated monomer (XIII) was set polymerizing in the same manner as in Example 1 four hours after preparation. The resultant polymer was treated in the same manner as in Example 1 to obtain an absorbent resin of acrylate (19). The physical properties of this absorbent resin are shown in Table 1.

EXAMPLE 20

A water-soluble unsaturated monomer (XIV) of a concentration of 34% having a β-hydroxy propionic acid content of 50 ppm and a ratio of neutralization of 90% was obtained by following the procedure of Example 1, except that the acrylate (XIV) was used instead of the acrylate (I) in the preparation of water-soluble unsaturated monomer.

The water-soluble unsaturated monomer (XIV) was set polymerizing in the same manner as in Example 1 24 hours after preparation and then treated in the same manner as in Example 1 to obtain an absorbent resin of acrylate (20). The physical properties of this resin are shown in Table 1.

EXAMPLE 21

In a switching cast polymerization device made of stainless steel (SUS 316), lined with ethylene tetrafluoride resin, and having an inner volume of 300 mm×300 mm×50 mm, 4,000 g of a water-soluble unsaturated monomer (XV) having a β-hydroxy propionic acid content of 290 ppm was placed in its unmodified form as an acrylate (XV) and the entrapped gas in the device was displaced with nitrogen. The device containing the acrylate (XV) was immersed in a water bath at 30° C.

After the elapse of 24 hours following the completion of the preparation of the acrylate, 0.05 mol % of ammonium persulfate and 0.02 mol % of sodium hydrogen sulfite were added to the acrylate to effect polymerization thereof. Five hours after the start of the polymerization, the hydrogel polymer consequently formed was removed from the cast polymerization device. The polymer was cut into cords by using a meat chopper and then dried and pulverized in the same manner as in Example 1 to obtain a water-soluble resin of acrylate (20). The results of the analysis of this water-soluble resin (20) are shown in Table 1.

EXAMPLE 22

One hundred (100) parts of the absorbent resin (1) obtained in Example 1 was mixed with 1 part of glycerol, 2 parts of water, and 2 parts of ethyl alcohol. The resultant mixture was heated at 190° C. for 20 minutes. The absorbent resin (22) consequently obtained was tested for absorption capacity, residual acrylic acid content, suction power, presence or absence of the formation of wetted clusters of powder, and increase of residual monomer content at surface cross-linking. The results of the test are shown in Table 3.

EXAMPLE 23

An absorbent resin (23) was obtained by mixing 100 parts by weight of the absorbent resin (5) with 0.1 part of ethylene glycol diglycidyl ether, 5 parts of water, and 1 part of isopropyl alcohol and heating the resultant mixture at 180° C. for 30 minutes. The results of the analysis of this absorbent resin (23) are shown in Table 3.

EXAMPLE 24

An absorbent resin (24) was obtained by mixing 100 parts of the absorbent resin (6) with 0.5 part of diethylene glycol, 2 parts of water, and 1 part of isopropyl alcohol and heating the resultant mixture at 150° C. for three hours. The results of the analysis of this absorbent resin (24) are shown in Table 3.

EXAMPLE 25

An absorbent resin (25) was obtained by dispersing 100 parts by weight of the absorbent resin (8) in a mixed solvent containing 300 parts of methanol and 30 parts of water, mixing the resultant dispersion with 0.1 parts of ethylene glycol diglycidyl ether, and heating the resultant dispersed mixture at 160° C. for 1 hour to effect evaporation to dryn. The results of the analysis of this resin (25) are shown in Table 3.

EXAMPLE 26

An absorbent resin (26) was obtained by adding 2.5 parts of ethylene carbonate, 2.5 parts of water, and 2.5 parts of acetone to 100 parts of the absorbent resin (9) and heating the resultant mixture at 180° C. for 1 hour. The results of the analysis of this absorbent resin (26) are shown in Table 3.

EXAMPLE 27

An absorbent resin (27) was obtained by mixing 100 parts by weight of the absorbent resin (11) with 1 part of finely divided silicon dioxide powder (Aerosil) and further with a treating solution containing 0.1 parts of ethylene glycol diglycidyl ether and 10 parts of water and heating the resultant mixture at 150° C. for 1 hour. The results of the analysis of this absorbent resin (27) are shown in Table 3.

EXAMPLE 28

An absorbent resin (28) was obtained by mixing 100 parts by weight of the absorbent resin (12) with 1 part of aluminum sulfate, 1 part of glycerin, and 8 parts of water and heating the resultant mixture at 180° C. for 30 minutes. The results of the analysis of the absorbent resin (28) are shown in Table 3.

EXAMPLE 29

The absorbent resin (18) was dispersed in 250 ml of cyclo-hexane. Separately, a dispersion of ethylene glycol diglycidyl ether was obtained in a flask by dissolving 0.5 g of sorbitan monolaurate (HLB=8.6, produced by Kao Soap Co., Ltd. and marketed under trademark designation of "Reodol SP-10") as a surfactant in 50 g of cyclohexane and adding an aqueous solution of 0.04 g of ethylene glycol diglycidyl ether in 2 ml of water with vigorous agitation to the dispersion. The droplets in this dispersion had an average particle diameter of 3 microns. An absorbent resin (29) was obtained by mixing this dispersion in a stirred state with a suspension of the absorbent resin (18), keeping the temperature of the system at 75° C. for 3 hours, separating the produced polymer by filtration, and drying the separated polymer under a vacuum.

Controls 1 to 3

Water-soluble unsaturated monomers (I) to (III) having β-hydroxy propionic acid contents respectively of 2,500 ppm, 4,200 ppm, and 8,200 ppm were obtained by following the procedure of Example 1, except that the acrylates (I) to (III) for comparison were used in the place of acrylate (I) in the preparation of the water-soluble unsaturated monomer. The water-soluble unsaturated monomers (I) to (III) for comparison were treated in the same manner as in Example 1 to produce absorbent resin of acrylate (1) to (3). The physical properties of these absorbent resins are shown in Table 2.

Controls 4 to 6

Absorbent resins of acrylate (4) to (6) for comparison were obtained by repeating the procedure of Control 1, except that the time intervening between the preparation of the water-soluble monomer (I) for comparison and the initiation of polymerization was increased respectively to 12 hours, 24 hours, and 240 hours. The physical properties of these absorbent resins (4) to (6) for comparison are shown in Table 2.

Controls 7 to 9

Water-soluble unsaturated monomers (IV) to (VI) for comparison having β-hydroxy propionic acid contents respectively of 1,100 ppm, 1,900 ppm, and 1,300 ppm were obtained by repeating the procedure of Example 8, except that the acrylates (IV) to (VI) for comparison were used in the place of acrylate (V) in the preparation of the water-soluble unsaturated monomer. The water-soluble unsaturated monomers (IV) to (VI) for comparison were treated in the same manner as in Example 8 to obtain absorbent resins of acrylate (7) to (9) for comparison. The physical properties of these absorbent resins are shown in Table 2.

Controls 10 to 12

Water-soluble unsaturated monomers (VII) to (IX) for comparison having β-hydroxy propionic acid contents respectively of 1,300 ppm, 2,100 ppm, and 3,300 ppm were obtained by repeating the procedure of Example 8, except that the acrylates (VII) to (IX) for comparison were used in instead of the acrylate (VIII) in the preparation of water-soluble unsaturated monomer. The water-soluble unsaturated monomers (VII) to (IX) for comparison were treated in the same manner as in Example 11 to obtain absorbent resins of acrylate (10) to (12) for comparison. The physical properties of these absorbent resins are shown in Table 2.

Control 13

A water-soluble unsaturated monomer (X) for comparison having a β-hydroxy propionic acid content of 6,700 ppm was obtained by repeating the procedure of Example 14, except that the acrylate (X) for comparison was used instead of the acrylate (XI) in the preparation of water-soluble unsaturated monomer. The water-soluble unsaturated monomer (X) for comparison was treated in the same manner as in Example 14 to obtain an absorbent resin of acrylate (13) for comparison. The physical properties of this absorbent resin are shown in Table 2.

Control 14

A water-soluble unsaturated monomer (XI) for comparison having a β-hydroxy propionic acid content of 2,100 ppm was obtained by repeating the procedure of Example 15, except that the acrylate (XI) for comparison was used instead of acrylate (XI) in the preparation of the water-soluble unsaturated monomer. The water-soluble unsaturated monomer (XI) for comparison was treated in the same manner as in Example 15 to obtain an absorbent resin of acrylate (14) for comparison. The physical properties of this absorbent resin are shown in Table 2.

Controls 15 and 16

Absorbent resins of acrylate for comparison (15) and (16) were obtained by repeating the procedure of Control 14, except that the water-soluble unsaturated monomer (XI) prepared in Control 14 was stored at 30° C. respectively for 24 hours and 120 hours before polymerization. The physical properties of these absorbent resins are shown in Table 2.

Control 17

A water-soluble unsaturated monomer (XII) for comparison having a β-hydroxy propionic acid content of 1,800 ppm was obtained by repeating the procedure of Example 19, except that acrylate (XII) for comparison was used instead of acrylate (XIII) in the preparation of water-soluble unsaturated monomer. The water-soluble unsaturated monomer (XII) was treated in the same manner as in Example 19 to obtain an absorbent resin of acrylate (17) for comparison. The physical properties of this absorbent resin are shown in Table 2.

Control 18

A water-soluble unsaturated monomer (XIII) for comparison having a β-hydroxy propionic acid content of 3,200 ppm was obtained by following the procedure of Example 21, except that the acrylate (XIII) for comparison was used instead of the acrylate (XV) in the preparation of water-soluble unsaturated monomer. The water-soluble unsaturated monomer (XIII) was treated in the same manner as in Example 21 to obtain an absorbent resin of acrylate (28) for comparison. The physical properties of this absorbent resin are shown in Table 2.

Control 19

A water-soluble unsaturated monomer (XIV) for comparison having a β-hydroxy propionic acid content of 2,800 ppm was obtained by repeating the procedure of Example 21, except that 2,590 ppm of β-hydroxy propionic acid was separately added to acrylate (XV). The water-soluble unsaturated monomer (XIV) was treated in the same manner as in Example 21 to obtain an absorbent resin of acrylate (19) for comparison. The physical properties of this absorbent resin are shown in Table 2.

Controls 20 to 22

Absorbent resins (20) to (22) for comparison were obtained by repeating the procedures of Examples 22 to 24, except that absorbent resins (1), (5) and (6) for comparison were used instead of absorbent resins (1) to (3) as absorbent resins for cross-linking surface regions thereof. The physical properties of these absorbent resins are shown in Table 2.

Controls 23 and 24

Absorbent resins (23) and (24) for comparison were obtained by repeating the procedures of Examples 25 and 26, except that an absorbent resins (7) and (8) for comparison were used instead of absorbent resins (8) and (9) for cross-linking the surface regions. The physical properties of these absorbent resins are shown in Table 3.

Controls 25 and 26

Absorbent resins (25) and (26) for comparison were obtained by repeating the procedures of Examples 27 and 28, except that absorbent resins (11) and (12) for comparison were used instead of absorbent resins (11) and (12) in cross-linking surface regions. The physical properties of these absorbent resins are shown in Table 3.

Analyzed results of acrylic acid salt polymers obtained in Examples 1 to 21 and Controls 1–19 are shown in Tables 1 and 2 and analyzed results of acrylic acid salt polymers wherein surface region is cross-linked obtained in Examples 22 to 29 and Controls 20 to 26 are shown in Table 3.

Further, the acrylic acid salt polymers obtained from the water-soluble unsaturated monomer containing not more than 100 ppm of β-hydroxy propionic acid in Examples contained not more than 100 ppm of β-hydroxy propionic acid, while the polymer obtained in Controls contained not less than 1000 ppm of β-hydroxy propionic acid.

TABLE 1

| | Resin obtained | Water-soluble unsaturated monomer used | β-hydroxy propionic acid content in monomer (ppm) | Time of standing after monomer preparation (hr) | Absorption capacity (g/g) | Residual monomer (ppm) | Latent residual monomer (ppm) |
|---|---|---|---|---|---|---|---|
| Example 1 | Absorbent resin (1) | Monomer (I) | 40 | 2 | 51 | 35 | max. 5 |
| " 2 | " (2) | " | 40 | 6 | 51 | 55 | " |
| " 3 | " (3) | " | 40 | 12 | 51 | 80 | " |
| " 4 | " (4) | " | 40 | 24 | 50 | 130 | " |
| " 5 | " (5) | (II) | 90 | 2 | 51 | 45 | " |
| " 6 | " (6) | (III) | 190 | 2 | 51 | 60 | 15 |
| " 7 | " (7) | (IV) | 100 | 2 | 51 | 45 | 10 |
| " 8 | " (8) | (V) | 50 | 6 | 64 | 80 | max. 5 |
| " 9 | " (9) | (VI) | 80 | 6 | 64 | 90 | 10 |
| " 10 | " (10) | (VII) | 130 | 6 | 64 | 110 | 10 |
| " 11 | " (11) | (VIII) | 230 | 2 | 40 | 140 | 30 |
| " 12 | " (12) | (IX) | 290 | 2 | 40 | 150 | 30 |
| " 13 | " (13) | (X) | 390 | 2 | 40 | 160 | 40 |
| " 14 | " (14) | (XI) | 230 | 3 | 70 | 220 | 20 |
| " 15 | " (15) | (XII) | 70 | 2 | 43 | 220 | max. 5 |

TABLE 1-continued

| Resin obtained | Water-soluble unsaturated monomer used | β-hydroxy propionic acid content in monomer (ppm) | Time of standing after monomer preparation (hr) | Absorption capacity (g/g) | Residual monomer (ppm) | Latent residual monomer (ppm) |
|---|---|---|---|---|---|---|
| " 16 | " (16) | " | 70 | 12 | 43 | 260 | " |
| " 17 | " (17) | " | 70 | 24 | 43 | 300 | " |
| " 18 | " (18) | (XII') | 70 | 2 | 75 | 60 | " |
| " 19 | " (19) | (XIII) | 35 | 4 | 42 | 40 | " |
| " 20 | " (20) | (XIV) | 50 | 24 | 52 | 50 | " |
| " 21 | water-soluble resin (21) | (XV) | 290 | 24 | — | 300 | 30 |

TABLE 2

| | Resin obtained | Water-soluble unsaturated monomer used | β-hydroxy propionic acid content in monomer (ppm) | Time of standing after monomer preparation (hr) | Absorption capacity (g/g) | Residual monomer (ppm) | Latent residual monomer (ppm) |
|---|---|---|---|---|---|---|---|
| Control 1 | Absorbent resin (1) | Monomer (I) | 2500 | 2 | 49 | 420 | 420 |
| " 2 | " (2) | (II) | 4200 | 2 | 48 | 700 | 870 |
| " 3 | " (3) | (III) | 8200 | 2 | 48 | 870 | 1200 |
| " 4 | " (4) | (I) | 2500 | 12 | 49 | 470 | 450 |
| " 5 | " (5) | " | 2500 | 24 | 49 | 560 | 460 |
| " 6 | " (6) | " | 2500 | 240 | 47 | 1560 | 480 |
| " 7 | " (7) | (IV) | 1100 | 6 | 63 | 300 | 140 |
| " 8 | " (8) | (V) | 1900 | 6 | 63 | 440 | 250 |
| " 9 | " (9) | (VI) | 1300 | 6 | 63 | 340 | 130 |
| " 10 | " (10) | (VII) | 1300 | 2 | 39 | 490 | 140 |
| " 11 | " (11) | (VIII) | 2100 | 2 | 38 | 550 | 240 |
| " 12 | " (12) | (IX) | 3300 | 2 | 38 | 730 | 410 |
| " 13 | " (13) | (X) | 6700 | 3 | 67 | 420 | 900 |
| " 14 | " (14) | (XI) | 2100 | 2 | 42 | 420 | 240 |
| " 15 | " (15) | " | 2100 | 24 | 42 | 830 | 320 |
| " 16 | " (16) | " | 2100 | 120 | 41 | 930 | 330 |
| " 17 | " (17) | (XII) | 1800 | 4 | 40 | 1300 | 340 |
| " 18 | water-soluble resin (18) | (XIII) | 3200 | 24 | — | 600 | 450 |
| " 19 | " (19) | (XIV) | 2800 | 24 | — | 670 | 510 |

TABLE 3

| | Absorbent resin obtained | Absorbent resin subjected to surface cross-linking | β-hydroxy propionic acid content in monomer (ppm) | Absorption capacity (g/g) | Residual monomer (ppm) | Suction power (g/g) | Increment to residual monomer content by surface cross-linking (ppm) | Increment to residual monomer by heating at 180° C. for three hours (ppm) |
|---|---|---|---|---|---|---|---|---|
| Example 22 | Absorbent (22) | (1) | 40 | 52 | 35 | 17.3 | 5> | max. 5 |
| " 23 | resin (23) | (5) | 90 | 53 | 45 | 17.2 | 5> | " |
| " 24 | (24) | (6) | 190 | 51 | 65 | 17.0 | 5 | " |
| " 25 | (25) | (8) | 50 | 66 | 80 | 16.8 | 5> | max. 5 |
| " 26 | (26) | (9) | 80 | 64 | 90 | 16.7 | " | " |
| " 27 | (27) | (11) | 230 | 41 | 150 | 16.2 | 10 | 30 |
| " 28 | (28) | (12) | 290 | 42 | 160 | 16.2 | 10 | 30 |
| " 29 | (29) | (18) | 70 | 77 | 60 | 16.0 | 5> | 5 |
| Control 20 | Absorbent (20) | for control (1) | 2500 | 49 | 460 | 16.8 | 40 | 400 |
| " 21 | resin for (21) | (2) | 4200 | 49 | 800 | 16.7 | 100 | 820 |
| " 22 | control (22) | (3) | 8200 | 48 | 1080 | 16.5 | 210 | 1000 |
| " 23 | (23) | (7) | 1100 | 63 | 390 | 16.3 | 90 | 120 |
| " 24 | (24) | (8) | 1900 | 62 | 560 | 16.5 | 120 | 210 |
| " 25 | (25) | (11) | 2100 | 38 | 660 | 15.7 | 110 | 190 |
| " 26 | (26) | (12) | 3300 | 39 | 980 | 15.9 | 250 | 250 |

Production 16

A sample of acrylic acid obtained from the site of acrylic acid production at Himeji Plant of Nippon Shokubai Kagaku Kogyo Co., Ltd. was refined by distillation. The acrylic acid fresh from the distillation was stored at 30° C. for two hours and then neutralized by the procedure disclosed in EP-A-0372706.

A distillation flask provided with a stirrer was charged with 1,944 g of deionized water. With the temperature of the neutralization reaction system in the flask kept at a level in the range of 20° C. to 40° C., 1,390 g of acrylic acid and 1,480 g of an aqueous 48 wt % sodium hydroxide solution were added simultaneously at a sodium hydroxide/acrylic acid dropping ratio in the range of 0.9 to 0.95 over a period of 100 minutes into the flask. After the completion of the dropwise addition, 160 g of an aqueous 48 wt % sodium hydroxide solution was supplied to adjust the ratio of neutralization of the neutralization reaction system in the flask to 102 mol %. Then, the temperature of the neutralization reaction system was adjusted to 40° C. and the product of neutralization was left to age for 30 minutes. After the completion of aging, 28 g of acrylic acid was supplied over a period of 1 minute to the neutralization reaction system to obtain 5,002 g of an acrylate (XVI) of a concentration of 37% having a ratio of neutralization of 100 mol %.

A monomer (1) of a concentration of 38% having a ratio of neutralization of 75% (55% of sodium salt and 20% of ammonium salt) was obtained by adding 774 g of acrylic acid aged for 2 hours after distillation and 1,063 g of deionized water to 3,338 g of acrylate (XVI) resulting from neutralization and adding 325 g of an aqueous 25% ammonia solution thereto, and further adding thereto 2.83 g (0.04 mol % based on the monomer) of trimethylol propane triacrylate as a cross-linking agent. The monomer (1), on being analyzed by liquid chromatography, was found to have a β-hydroxy propionic acid content of 25 ppm.

Production 17

A monomer (2) of a concentration of 38% having a ratio of neutralization of 75% (35% of sodium salt and 40% of ammonium salt) was obtained by repeating the procedure for the production of the acrylate (XVI) in the preparation of the monomer in Production 16, except that 2,148 g of acrylate (XVI), 1,132 g of acrylic acid, 1,563 g of deionized water, 657 g of an aqueous 25% ammonia solution, and 2.86 g (0.04 mol % based on the monomer) of trimethylol propane triacrylate were used instead. The β-hydroxy propionic acid content in the monomer (2) was found to be 18 ppm.

Production 18

A monomer (3) of a concentration of 38% having a ratio of neutralization of 75% (65% of sodium salt and 10% of ammonium salt) was obtained by following the procedure for the production of the acrylate (XVI) in the preparation of the monomer in Production 16, except that 3,922 g of acrylate (XVI), 599 g of acrylic acid, 817 g of deionized water, 162 g of an aqueous 25% ammonia solution, and 2.81 g (0.04 mol % based on the monomer) of trimethylol propane triacrylate were used instead. The β-hydroxy propionic acid content in the monomer (3) was found to be 22 ppm.

Production 19

An acrylate (XVII) was obtained by following the procedure of. Production 16, except that acrylic acid aged for 12 hours after being refined by distillation was used instead of the refined acid aged for 2 hours in the preparation of the acrylate and monomer. A monomer (4) of a concentration of 38% having a ratio of neutralization of 75% (55% of sodium salt and 20% of ammonium salt) was obtained by repeating the procedure of Production 1 using the acrylate (XVII) instead. The β-hydroxy propionic acid content in the monomer (4) was found to be 50 ppm.

Production 20

An acrylate (XVIII) was obtained by following the procedure of Production 16, except that acrylic acid aged for 24 hours after being refined by distillation was used instead of acrylic acid aged for two hours after distillation in the preparation of the acrylate and monomer. A monomer (5) of a concentration of 38% having a ratio of neutralization of 75% (55% of sodium salt and 20% of ammonium salt) was obtained by following the procedure of Production 1 using acrylate (XVIII) instead. The β-hydroxy propionic acid content in the monomer (5) was found to be 110 ppm.

Production 21

A commercially available acrylic acid (guaranteed reagent produced by Wako Junyaku K.K.) was refined by distillation. The refined acrylic acid was converted into an aqueous 80% solution having a high point of solidification thereby allowing easy handling. The solution was stored at a temperature of 30° C. for two hours and then neutralized by the following procedure.

A distillation flask provided with a stirrer was charged with 2,272 g of deionized water and 1,640 g of an aqueous 48 wt % sodium hydroxide solution. Then, with the temperature of the neutralization reaction system kept at 10° C., 2,361 g of an aqueous 80% acrylic acid solution was supplied meanwhile over a period of 6 hours to the flask to obtain an acrylate (XIX) of a concentration of 37% having a ratio of neutralization of 75 mol %.

Then, a monomer (6) of a concentration of 38% having a ratio of neutralization of 75% (55% of sodium salt and 20% of ammonium salt) was obtained by repeating the procedure of Production 16 using acrylate (XIX) instead. The β-hydroxy propionic acid content in the monomer (6) was found to be 50 ppm.

Production 22

A monomer (7) of a concentration of 38% having a ratio of neutralization of 75% (75% of sodium salt) was obtained by repeating the procedure of Production 16, except that 4,500 g of acrylate (XVI), 425 g of acrylic acid, 575 g of deionized water, and 3.39 g (0.03 mol % based on the monomer) of polyethylene glycol diacrylate (average n=7) were used in the same manner as the production of acrylate (XVI) in the preparation of the monomer. The β-hydroxy propionic acid content in the monomer (7) was found to be 30 ppm.

Control Production 14

An acrylate (XIV) for comparison was obtained by repeating the procedure of Production 16, except that acrylic acid aged for 200 hours after being refined by distillation was used instead of refined acrylic acid aged for 2 hours in the production of the acrylate and monomer in the preparation of the monomer. A monomer (1) for comparison of a concentration of 38% having a ratio of neutral-ization of 75% (55% of sodium salt and 20% of ammonium salt) was obtained by following the procedure of Example 16 of Production using the acrylate (XIV) for comparison instead. The β-hydroxy propionic acid content in the monomer (1) for comparison was found to be 1,100 ppm.

Production 15

An acrylate (XV) for comparison was obtained by repeating the procedure of Production 16, except that a commercially available acrylic acid (guaranteed reagent produced by Wako Junyaku K.K.) was used in its unmodified form instead of refined acrylic acid aged for two hours in the production of the acrylate and monomer in the preparation of the monomer. A monomer (2) for comparison of a concentration of 38% having a ratio of neutralization of 75% (55% of sodium salt and 20% of ammonium salt) was obtained by using the acrylate (XV) for comparison. The β-hydroxy propionic acid content in the monomer (2) for comparison was found to be 3,200 ppm.

Control Production 16

An acrylate (XVI) for comparison was obtained by following the procedure of Production 21, except that the temperature of the neutralization reaction system was raised from 10° C. to a level in the range of 50° to 60° C. for the purpose of reducing the duration of neutralization. The time required for the neutralization consequently decreased from six hours to 40 minutes. Then, a monomer (3) for comparison of a concentration of 38% having a ratio of neutralization of 75% (55% of sodium salt and 20% of ammonium salt) was obtained by following the procedure of Production 16 using acrylate (XVI) instead. The β-hydroxy propionic acid content in the monomer (5) was found to be 1,300 ppm.

Control Production 17

A monomer (4) for comparison was obtained by repeating the procedure of Production 22, except that an aqueous acrylic acid solution stored for 200 hours after being refined by distillation was used as an aqueous 80% acrylic acid solution for the neutralization. The β-hydroxy propionic acid content in the monomer (4) for comparison was found to be 2,900 ppm.

Control Production 18

A monomer (5) for comparison having a β-hydroxy propionic acid content of 1,600 ppm was obtained by repeating the procedure of Production 22, except that the same acrylic acid as used in Control Production 14 was used instead of the acrylic acid aged for two hours after distillation in the preparation of the monomer.

EXAMPLE 30

In a reaction vessel constructed by fitting a lid to a jacketed twin-arm type kneader made of stainless steel, having an inner volume of 10 liters, and provided with two sigma type vanes, 5,500 g of the monomer (1) obtained in Production 16 deaerated with nitrogen gas for 30 minutes was placed. Then, with the reaction vessel kept heated by passage of hot water at 35° C. through the jacket, 0.3 mol % of ammonium persulfate and 0.03 mol % of sodium hydrogen sulfite were added to the reaction vessel. Two hours had elapsed between the time the monomer was prepared by the procedure described above and the time polymerization was initiated by the addition of an initiator. Polymerization was initiated 1 minute after the addition of the initiator. The gel polymer consequently formed was finely divided into particles about 5 mm in diameter in 16 minutes. The stirring continued for a further 44 minutes before the gel polymer was removed from the reaction vessel.

The minute particles of the gel polymer consequently obtained were spread on a 50-mesh metallic net and then heat-treated thereon at 180° C. for 60 minutes with the aid of hot air. The dry particles thus formed were pulverized with a vibration mill and then classified with a 20-mesh screen to obtain an absorbent resin (30). The results are shown in Table 4.

EXAMPLES 31 AND 32

Absorbent resins (31) and (32) were obtained by repeating the procedure of Example 30, except that the time between the completion of the preparation of the monomer (a) and the introduction of the initiator was changed respectively to six hours and 24 hours. The results are shown in Table 4.

EXAMPLES 33 AND 34

Absorbent resins (33) and (34) were obtained by repeating the procedure of Example 30, except that the temperature for drying and heating the gel polymer resulting from polymerization was changed respectively to 150° C. and 120° C. The results are shown in Table 4. It is clearly noted from the data of Table 4 that the absorption ratio was lowered and the residual monomer content was increased by lowering the temperature of drying.

EXAMPLES 35 TO 38

Absorbent resins (35) to (38) were obtained by repeating the procedure of Example 16, except that the monomers (2) to (5) were used instead of monomer (1) for polymerization. The results are shown in Table 4.

EXAMPLE 39

In a switching cast polymerization device made of stainless steel (SUS 316), lined with ethylene tetrafluoride resin, and having an inner volume of 300 mm×300 mm×50 mm, 4,000 g of monomer (6) deaerated with nitrogen was placed and the entrapped gas in the device was displaced with nitrogen. The device containing the monomer was immersed in a water bath kept at 30° C. Then, 0.05 mol % of ammonium persulfate and 0.02 mol % of sodium hydrogen sulfite were added to the device to initiate polymerization. Four hours had elapsed between the time the monomer (6) was prepared by the procedure described above and the time the polymerization was initiated.

After 5 hours from the start of the polymerization, the gel polymer consequently formed was withdrawn from the cast polymerization device. The gel polymer was then pulverized into particles about 5 mm in diameter by using a meat chopper and dried and heat-treated in the same manner as in Example 1 to obtain an absorbent resin (39). The results are shown in Table 4.

EXAMPLE 40

The procedure of Example 30 was repeated to polymerize monomer (7) instead of monomer (1). The gel polymer which was formed within 30 minutes of commencing the polymerization was combined with 160 g (10 mol % based on the monomer) of an aqueous 25% ammonia solution and subjected to continued polymerization for 30 minutes. The resultant gel polymer having a ratio of neutralization of 85% (inclusive of 10 mol % of ammonium salt) was dried at 170° C. for 80 minutes with the aid of hot air and thereafter treated in the same manner as in Example 1 to obtain an absorbent resin (40). The results are shown in Table 4.

EXAMPLE 41

The procedure of Example 30 was repeated to polymerize a monomer formed of monomer (7) and 142 g (10 mol % based on the monomer) of urea as an ammonia precursor instead of monomer (1). The resultant gel polymer having a ratio of neutralization of 95% (inclusive of 20 mol % of ammonium salt) was dried at 190° C. for 60 minutes with the aid of hot air and thereafter treated in the same manner as in Example 30 to obtain an absorbent resin (41). The results are shown in Table 4.

EXAMPLE 42

An absorbent resin (42) was obtained by mixing 100 parts of absorbent resin (30) powder obtained in Example 30 with 1 part of glycerol, 2 parts of water, and 2 parts of ethyl alcohol and then heat-treating the resultant mixture at 190° C. for 40 minutes. The results are shown in Table 5.

EXAMPLE 43

An absorbent resin (43) was obtained by mixing 100 parts of absorbent resin (35) powder with 2 parts of propylene glycol, 3 parts of water, and 2 parts of isopropyl alcohol and then heat-treating the resultant mixture at 150° C. for 60 minutes. The results are shown in Table 5.

EXAMPLE 44

An absorbent resin (44) was obtained by mixing 100 parts of absorbent resin (36) powder with 0.1 part of ethylene glycol diglycidyl ether, 5 parts of water, and 1 part of isopropyl alcohol and then heat-treating the resultant mixture at 180° C. for 30 minutes. The results are shown in Table 5.

EXAMPLE 45

An absorbent resin (45) was obtained by mixing 100 parts of absorbent resin (37) powder with 0.1 part of ethylene glycol diglycidyl ether, 30 parts of methanol, and 15 parts of water and then heat-treating the resultant mixture at 180° C. for one hour. The results are shown in Table 5.

EXAMPLE 46

An absorbent resin (46) was obtained by mixing 100 parts of absorbent resin (38) powder with 2.5 parts of ethylene carbonate, 2.5 parts of water, and 2.5 parts of acetone and then heat-treating the resultant mixture at 230° C. for one hour. The results are shown in Table 5.

EXAMPLE 47

An absorbent resin (47) was obtained by mixing 100 parts of absorbent resin (39) powder with 0.1 part of ethylene glycol diglycidyl ether and 10 parts of water in the presence of 1 part of fine silicon dioxide powder (Aerosil) and then heat-treating the resultant mixture at 180° C. for one hour. The results are shown in Table 5.

EXAMPLE 48

An absorbent resin (48) was obtained by mixing 100 parts by weight of absorbent resin (4) powder with 1 part of aluminum sulfate, 1 part of glycerol, and 8 parts of water, and heat-treating the resultant mixture at 180° C. for 30 minutes. The results are shown in Table 2.

Control 27

An absorbent resin (27) for comparison was obtained by repeating the procedure of Example 30, except that monomer (1) for comparison was used instead of monomer (1). The results are shown in Table 4.

Control 28

An absorbent resin (28) for comparison was obtained by repeating the procedure of Control 27, except that the time between the completion of the preparation of monomer (1) for comparison and the introduction of the initiator was changed to 24 hours. The results are shown in Table 4.

Control 29

An absorbent resin (29) for comparison was obtained by repeating the procedure of Control 27, except that the temperature for drying and heat-treating the gel polymer resulting from polymerization was changed to 120° C. The results are shown in Table 1.

Controls 30 to 33

Absorbent resins (30) to (33) for comparison were obtained by repeating the procedure of Example 30, except that monomers (2) to (5) for comparison were used respectively instead of monomer (1). The results are shown in Table 4.

Control 34

An absorbent resin (34) for comparison was obtained by repeating the procedure of Example 42, except that a powder of absorbent resin (27) for comparison was used instead of absorbent resin (30) powder for the purpose of cross-linking the surface region. The results are shown in Table 5.

Controls 35 to 38

Absorbent resins (35) to (38) for comparison were obtained by repeating the procedures of Examples 43 to 46 respectively, except that powders of absorbent resins (30) to (33) for comparison were used instead of absorbent resins (35) to (38). for the purpose of cross-linking surface regions. The results are shown in Table 5.

It is clearly noted from the data of Table 4 and Table 5 that an absorbent resin produced by the method according to this invention has only a small residual monomer content and allows neither generation nor growth of residual monomer as a consequence of surface treatment or a subsequent heat treatment. Further, due to the heat treatment which is performed at an elevated temperature, the produced absorbent resin has a high absorption capacity.

The acrylic acid salt polymers obtained from the water-soluble unsaturated-monomer containing not more than 100 ppm of β-hydroxy propionic acid in Examples contained not more than 100 ppm of β-hydroxy propionic acid, while the polymers obtained in Controls contained not less than 1000 ppm of β-hydroxy propionic acid.

TABLE 4

| | Absorbent resin obtained | Monomer used | β-hydroxy propionic acid content in monomer (ppm) | Time of standing after preparation of monomer (hr) | Temperature of heat treatment (° C.) | Absorption capacity (g/g) | Residual monomer content (ppm) | Increae or decrease inresidual monomer content by 3 hours heating at 180° C. (ppm) |
|---|---|---|---|---|---|---|---|---|
| Example | Absorbent resin | Monomer | | | | | | |
| ↑ 30 | ↑ (30) | (1) | 25 | 2 | 180 | 53 | 13 | −5 |
| ↑ 31 | ↑ (31) | ↑ | ↑ | 6 | ↑ | 53 | 15 | −4 |
| ↑ 32 | ↑ (32) | ↑ | ↑ | 24 | ↑ | 52 | 23 | −4 |
| ↑ 33 | ↑ (33) | ↑ | ↑ | 2 | 150 | 51 | 26 | −5 |
| ↑ 34 | ↑ (34) | ↑ | ↑ | ↑ | 120 | 44 | 55 | −20 |
| ↑ 35 | ↑ (35) | (2) | 18 | ↑ | 180 | 53 | 5 | −2 |
| ↑ 36 | ↑ (36) | (3) | 22 | ↑ | ↑ | 53 | 20 | ±0 |
| ↑ 37 | ↑ (37) | (4) | 50 | ↑ | ↑ | 53 | 19 | −7 |
| ↑ 38 | ↑ (38) | (5) | 110 | ↑ | ↑ | 52 | 28 | −10 |
| ↑ 39 | ↑ (39) | (6) | 50 | 4 | ↑ | 53 | 16 | −5 |
| ↑ 40 | ↑ (40) | (7) | 30 | 2 | 170 | 56 | 10 | ±0 |
| ↑ 41 | ↑ (41) | ↑ | ↑ | ↑ | 190 | 60 | 15 | −3 |
| Control | Absorbent resin for Control | Monomer for control | | | | | | |
| 27 | (27) | (1) | 1100 | 2 | 180 | 52 | 140 | +20 |
| ↑ 28 | ↑ (28) | ↑ | ↑ | 24 | ↑ | 51 | 150 | +10 |
| ↑ 29 | ↑ (29) | ↑ | ↑ | 2 | 120 | 43 | 320 | +20 |
| ↑ 30 | ↑ (30) | (2) | 3200 | ↑ | 180 | 51 | 290 | +40 |
| ↑ 31 | ↑ (31) | (3) | 1300 | ↑ | ↑ | 52 | 160 | +20 |
| ↑ 32 | ↑ (32) | (4) | 2900 | ↑ | ↑ | 51 | 430 | +50 |
| ↑ 33 | ↑ (33) | (5) | 1600 | ↑ | ↑ | 52 | 520 | +240 |

TABLE 5

| | Absorbent resin obtained | Absorbent resin subjected to surface cross-linking | β-hydroxy propionic acid content in monomer (ppm) | Temperature of heat treatment (° C.) | Absorption capacity (g/g) | Suction power (g/g) | Residual monomer content (ppm) | Increae or decrease inresidual monomer content due to surface cross-linking (ppm) |
|---|---|---|---|---|---|---|---|---|
| Example | Absorbent resin | Absorbent resin | | | | | | |
| ↑ 42 | ↑ (42) | (30) | 25 | 190 | 51 | 17.3 | 9 | −4 |
| ↑ 43 | ↑ (43) | ↑ (35) | 18 | 150 | 51 | 17.2 | 3 | −2 |
| ↑ 44 | ↑ (44) | ↑ (36) | 22 | 180 | 52 | 17.0 | 20 | ±0 |
| ↑ 45 | ↑ (45) | ↑ (37) | 50 | 180 | 48 | 16.7 | 16 | −3 |
| ↑ 46 | ↑ (46) | ↑ (38) | 110 | 230 | 50 | 16.9 | 20 | −8 |
| ↑ 47 | ↑ (47) | ↑ (39) | 50 | 180 | 51 | 16.5 | 14 | −2 |
| ↑ 48 | ↑ (48) | ↑ (40) | 30 | 180 | 53 | 16.2 | 10 | ±0 |
| Control | Absorbent resin for control | for control | | | | | | |
| 34 | (34) | (27) | 1100 | 190 | 49 | 16.8 | 150 | +10 |
| ↑ 35 | ↑ (35) | ↑ (30) | 3200 | 150 | 49 | 16.9 | 310 | +20 |
| ↑ 36 | ↑ (36) | ↑ (31) | 1300 | 180 | 50 | 16.5 | 170 | +10 |
| ↑ 37 | ↑ (37) | ↑ (32) | 2900 | 180 | 48 | 16.7 | 460 | +30 |
| ↑ 38 | ↑ (38) | ↑ (33) | 1600 | 230 | 49 | 16.8 | 580 | +60 |

The invention claimed is:

1. A method for the production of an acrylic acid salt-based polymer which comprises preparing a mixture solution of water-soluble unsaturated monomer or monomer mixture containing at least 50 mol % of acrylic acid partially or completely neutralized in an amount of 30 to 100 mol %, polymerizing said monomer or monomer mixture, and optionally drying the polymer to form the acrylic acid salt-based polymer, wherein said polymer is water-soluble and said polymerization is carried out by using the water-soluble unsaturated monomer or monomer mixture which contains from about 1 to about 1,000 ppm of β-hydroxy propionic acid or a salt thereof totally to said monomer or monomer mixture.

2. A method according to claim 1, wherein said water-soluble unsaturated monomer or monomer mixture is polymerized as a solution or an aqueous solution, and said acrylic acid salt-based polymer thus obtained is further dried at a temperature of 700 to 300° C.

3. A method according to claim 1, wherein said acrylic acid salt-based polymer, after optional drying, is further heat-treated at a temperature of 120° to 260° C.

4. A method according to claim 1, wherein acrylic acid is used within 24 hours after purification by distillation for neutralization or preparation of the water-soluble unsaturated monomer or monomer mixture.

5. A method according to claim 1, wherein a neutralization ratio of acrylic acid which exceeds 100 mol % occurs at least one time during the neutralization step of acrylic acid.

6. A method according to claim 1, wherein average particle diameter of said polymer is 10 to 2,000 μm.

7. A method according to claim 1, wherein average particle diameter of said polymer is 300 to 600 μm.

8. A method according to claim 1, wherein said water-soluble monomer or monomer mixture is polymerized within 24 hours after preparation.

9. A method according to claim 1, wherein total content of β-hydroxy propionic acid and a salt thereof is from about 1 to not more than 100 ppm.

10. A method according to claim 1, wherein said acrylic acid salt is sodium acrylate or potassium acrylate.

11. An acrylic salt-based polymer composition having not more than 100 ppm of a residual monomer content based on polymer, wherein said polymer comprises 50–100 mol % of an acrylic acid salt repeating unit and 0–50 mol % of another hydrophilic and/or hydrophobic monomer repeating unit, a neutralization ratio of carboxyl group is 30–100 mol %, and a total of β-propionic acid or salt thereof is 1–1000 ppm based on polymer.

12. A composition according to claim 11, wherein said acrylic acid salt polymer is an absorbent resin.

13. A composition according to claim 11, wherein the content of β-hydroxy propionic acid (salt) is 1 to 100 ppm.

14. A method according to claim 8, wherein said water-soluble monomer or monomer mixture is polymerized with a polymerization initiator.

15. A composition according to claim 11, wherein said acrylic acid salt-based polymer is water-soluble resin.

16. A composition according to claim 11, wherein average particle diameter of said polymer is 10 to 2,000 μm.

17. A composition according to claim 11, wherein average particle diameter of said polymer is 300 to 600 μm.

18. A composition according to claim 11, wherein said acrylic acid salt is sodium acrylate or potassium acrylate.

19. A composition according to claim 12, wherein said acrylic acid salt polymer has a cross-linked surface region.

* * * * *